United States Patent
Wadsworth et al.

(10) Patent No.: US 9,481,685 B2
(45) Date of Patent: *Nov. 1, 2016

(54) IMAGING NEUROINFLAMMATION

(75) Inventors: Harry John Wadsworth, Amersham (GB); Bo Shan, Jiangsu (CN); Dennis O'Shea, Amersham (GB); Joanna Marie Passmore, Amersham (GB); William John Trigg, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 355 days.

This patent is subject to a terminal disclaimer.

(21) Appl. No.: 13/119,450

(22) PCT Filed: Oct. 2, 2009

(86) PCT No.: PCT/EP2009/062827
§ 371 (c)(1),
(2), (4) Date: Mar. 17, 2011

(87) PCT Pub. No.: WO2010/037851
PCT Pub. Date: Apr. 8, 2010

(65) Prior Publication Data
US 2011/0190618 A1    Aug. 4, 2011

Related U.S. Application Data

(60) Provisional application No. 61/102,031, filed on Oct. 2, 2008.

(30) Foreign Application Priority Data

Oct. 13, 2008    (GB) .................................. 0818738.7

(51) Int. Cl.
| A61K 51/00 | (2006.01) |
| A61M 36/14 | (2006.01) |
| C07D 495/04 | (2006.01) |
| A61K 51/04 | (2006.01) |

(52) U.S. Cl.
CPC ......... C07D 495/04 (2013.01); A61K 51/0446 (2013.01)

(58) Field of Classification Search
CPC .................. C07D 495/04; A61K 51/0446
USPC ........................................ 424/1.89
See application file for complete search history.

(56) References Cited

U.S. PATENT DOCUMENTS

| 6,281,355 B1 | 8/2001 | Nakazato et al. |
| 6,870,069 B2 | 3/2005 | Suzuki et al. |

FOREIGN PATENT DOCUMENTS

| JP | 07-165721 | 6/1995 |
| WO | 99/51594 | 10/1999 |
| WO | 2007/057705 | 5/2007 |

OTHER PUBLICATIONS

Kozikowski et al. J. Med. Chem. 1993, 36, 2908-2920.*
Da Settimo et al. J. Med. Chem. 2008, 51, 5798-5806.*
Nakazato et al. "Design, Synthesis, and Structure-Activity Relationships of Novel Tetracyclic Compounds as Peripheral Benzodiazepine Receptor Ligands". Bioorganic & Medicinal Chemistry, vol. 12, 2004, pp. 3569-3580.
PCT/EP2009/062827 ISRWO Dated May 7, 2010.
GB 0818738.7 Search Report Dated Jan. 29, 2009.

* cited by examiner

*Primary Examiner* — Michael G Hartley
*Assistant Examiner* — Sean R Donohue
(74) *Attorney, Agent, or Firm* — Wood IP LLC

(57) ABSTRACT

The present invention concerns in vivo imaging and in particular in vivo imaging of the peripheral benzodiazepine receptor (PBR). A tetracyclic indole in vivo imaging agent is provided that binds with high affinity to PBR, has good uptake into the brain following administration, and which preferentially binds to tissues expressing higher levels of PBR. The present invention also provides a precursor compound useful in the synthesis of the in vivo imaging agent of the invention, as well as a method for synthesis of said in vivo imaging agent comprising use of said precursor compound, and a kit for carrying out said method. A cassette for the automated synthesis of the in vivo imaging agent is also provided. In addition, the invention provides a radiopharmaceutical composition comprising the in vivo imaging agent of the invention, as well as methods for the use of said in vivo imaging agent.

3 Claims, 2 Drawing Sheets

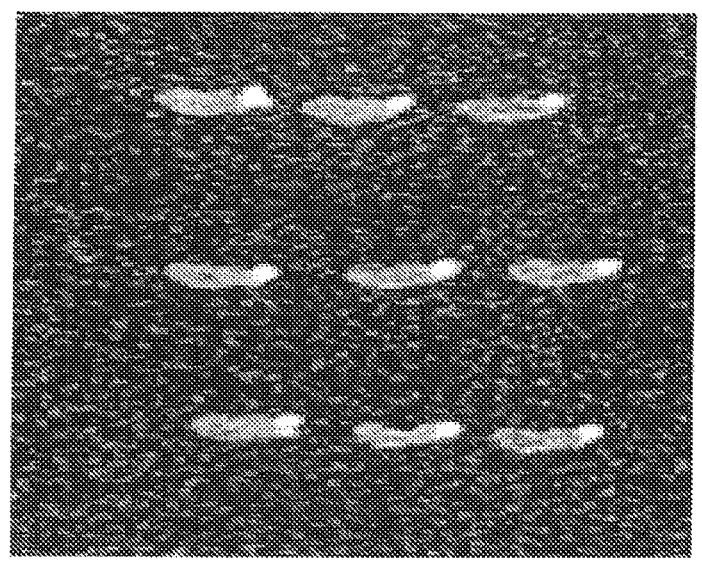
Figure 1: Representative autoradiographs showing binding of *in vivo* imaging agent 1 in the lesioned (right hand) facial nucleus of the FNA rat.

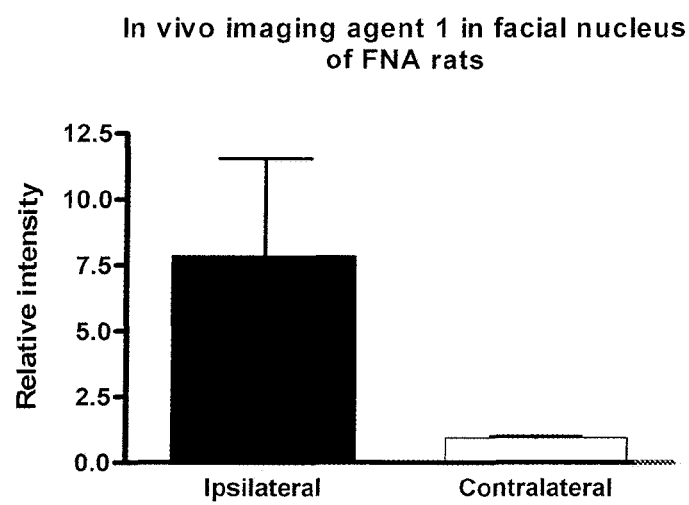
Figure 2: Relative intensity of *in vivo* imaging agent 1 binding in the facial nucleus of a rat seven days post-FNA. Data are expressed as mean ± SD of 24 individual sections from 1 animal.

IMAGING NEUROINFLAMMATION

This application is a filing under 35 U.S.C. 371 of international application no. PCT/EP2009/062827, filed Oct. 2, 2009, which claims priority to Great Britain application no. 0818738.7 filed Oct. 13, 2008 and U.S. application No. 61/102,031 filed Oct. 2, 2008, the entire disclosure of each of which is hereby incorporated by reference.

TECHNICAL FIELD OF THE INVENTION

The present invention concerns in vivo imaging and in particular in vivo imaging of the peripheral benzodiazepine receptor (PBR). A tetracyclic indole in vivo imaging agent is provided that binds with high affinity to PBR, has good uptake into the brain following administration, and which preferentially binds to tissues expressing higher levels of PBR. The present invention also provides a precursor compound useful in the synthesis of the in vivo imaging agent of the invention, as well as a method for synthesis of said in vivo imaging agent comprising use of said precursor compound, and a kit for carrying out said method. A cassette for the automated synthesis of the in vivo imaging agent is also provided. In addition, the invention provides a radiopharmaceutical composition comprising the in vivo imaging agent of the invention, as well as methods for the use of said in vivo imaging agent.

DESCRIPTION OF RELATED ART

The peripheral benzodiazepine receptor (PBR), which is also known as translocator protein (TSPO), is known to be mainly localised in peripheral tissues and glial cells but its physiological function remains to be clearly elucidated. Subcellularly, PBR is known to localise on the outer mitochondrial membrane, indicating a potential role in the modulation of mitochondrial function and in the immune system. It has furthermore been postulated that PBR is involved in cell proliferation, steroidogenesis, calcium flow and cellular respiration. PBR has been associated with a variety of conditions including acute and chronic stress, anxiety, depression, Parkinson's disease, Alzheimer's disease, brain damage, cancer (Gavish et al Pharm. Rev. 1999; 51: 629), Huntington's disease (Melβmer and Reynolds Neurosci. Lett. 1998; 241: 53-6), asthma (Pelaia et al Gen. Pharmacol. 1997; 28(4): 495-8), rheumatoid arthritis (Bribes et al Eur. J. Pharmacol. 2002; 452(1): 111-22), atherosclerosis (Davies et at J. Nucl. Med. 2004; 45: 1898-1907) and multiple sclerosis (Banati et al 2000 Brain; 123: 2321). PBR may also be associated with neuropathic pain, Tsuda et at having observed activated microglia in subjects with neuropathic pain (2005 TINS 28(2) pp 101-7).

Ligands having high affinity for PBR are known in the art. A class of indole compounds having affinity for PBR ($IC_{50}$ values for most active compounds of between 0.2 nM and 5.0 nM) is disclosed in U.S. Pat. No. 6,451,795. The compounds disclosed therein are stated to be useful for the prevention or treatment of peripheral neuropathies and for the treatment of central neurodegenerative diseases. Okubu et al (Bioorganic & Medicinal Chemistry 2004; 12: 3569-80) describe the design, synthesis and structure of a group of tetracyclic indole compounds having affinity for PBR ($IC_{50}$ values as low as about 0.4 nM). No particular application of the compounds is discussed in this publication by Okubu et al.

In vivo imaging of PBR is also known in the art. Positron emission tomography (PET) imaging using the PBR selective ligand, (R)-[$^{11}$C]PK11195 provides a generic indicator of central nervous system (CNS) inflammation. Despite the successful use of (R)—[$^{11}$C]PK11195, it has its limitations. It is known to have high protein binding, and low specific to non-specific binding (Lockhart et al. Nucl Med Biol. 30(2): 199-206). The role of its radiolabelled metabolites is not known and quantification of binding requires complex modelling. There have been efforts to provide compounds having high affinity and selectivity for PBR to enable improved measurement of PBR in the CNS. [$^{11}$C]DAA1106 and [$^{18}$F]FEDAA1106 are PET radioligands based on aryloxyalinine compounds and have been studied in humans (Ikomo et al J. Cereb. Blood Flow Metab. 2007; 27: 173-84 and Fujimura et al J. Nuc. Med. 2006; 47: 43-50). However, the kinetic properties of these compounds are not ideal and may limit their application to quantitative studies. In an effort to improve further upon these radioligands, another aryloxyaniline derivative, PBR28, has been reported by Briard et al (J. Med. Chem. 2008; 51: 17-30). An $^{11}$C-labelled version of PBR28 was injected into monkey to assess its brain kinetics using PET. [$^{11}$C]PBR28 showed high brain uptake, good specific binding to PBR-expressing tissues and kinetic properties more suitable for in vivo imaging. PBR-binding pyrazolopyrimidine compounds have also been evaluated as PET radioligands for targeting PBR. James et al (J. Nuc. Med. 2008; 49(5): 814-22) report that the PET radioligand [$^{18}$F]-DPA-714 has high affinity for PBR, and selective uptake by PBR in baboon brain following intravenous administration. The kinetics of brain uptake of [$^{18}$F]-DPA-714 was reported to be slower than, but similar in nature to, [$^{11}$C]DAA1106 and [$^{18}$F]FEDAA1106. WO 2007/057705 discloses tetracyclic indole compounds labelled with an imaging moiety, which are suitable for in vivo imaging. The in vivo imaging agents exemplified in WO 2007/057705 were shown to have good affinity to PBR, with $K_i$ values in a competition assay against [$^3$H]-PK-11195 of between 1.0 nM and 0.1 nM. However, the present inventors have now found that the selectivity of these compounds for PBR-expressing tissues is not ideal for in vivo imaging of PBR expression in the central nervous system.

There is scope to improve upon the known tetracyclic indole compounds in order to provide alternative in vivo imaging agents for evaluation of PBR expression in the central nervous system.

SUMMARY OF THE INVENTION

The present invention provides in vivo imaging agents based on tetracyclic indole compounds. In comparison to known in vivo imaging agents based on tetracyclic indole compounds, the in vivo imaging agents of the present invention have better properties for in vivo imaging. The in vivo imaging agents of the present invention have good binding properties to the peripheral benzodiazepine receptor, as well as good brain uptake and in vivo kinetics following administration to a subject.

DETAILED DESCRIPTION OF THE INVENTION

In Vivo Imaging Agent

In one aspect the present invention provides an in vivo imaging agent of Formula I:

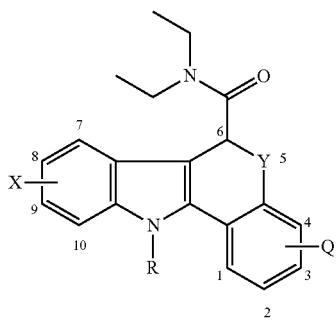

(I)

or a salt or solvate thereof wherein:
Q is hydrogen or fluorine;
X is hydrogen, fluoro, bromo, iodo, hydroxy, $C_{1-6}$ alkyl, $C_{1-6}$ haloalkyl, $C_{1-6}$ alkoxy, or $C_{1-6}$ alkyl amide;
Y is S, SO or $SO_2$; and,
R is hydrogen, $C_{1-6}$ alkyl, or $C_{1-6}$ fluoroalkyl;
and wherein at least one atom of said in vivo imaging agent of Formula I is a radioisotope suitable for in vivo imaging; wherein when said radioisotope is a radioisotope of carbon, it is a carbonyl carbon;
with the proviso that, when Y is S, Q or X are not both hydrogen.

The term "in vivo imaging" as used herein refers to those techniques that non-invasively produce images of all or part of the internal aspect of the subject of the invention. Preferred in vivo imaging methods for use in the present invention are single photon emission computed tomography (SPECT) and positron emission tomography (PET), with PET being especially preferred. The preference for PET in the method of the invention is due to its excellent sensitivity and resolution, so that even relatively small changes in a lesion can be observed over time. PET scanners routinely measure radioactivity concentrations in the picomolar range. Micro-PET scanners now approach a spatial resolution of about 1 mm, and clinical scanners about 4-5 mm.

The "in vivo imaging agent" of Formula I comprises a radioisotope suitable for in vivo imaging. This "radioisotope suitable for in vivo imaging" is a radioisotopic form of one of the atoms defined above for the in vivo imaging agent of Formula I. In order to be suitable for in vivo imaging as defined herein, the radioisotope is preferably a gamma- or a positron-emitter, thereby enabling detection of the in vivo imaging agent external to the subject following administration.

Suitable salts according to the invention include (i) physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids; and (ii) physiologically acceptable base salts such as ammonium salts, alkali metal salts (for example those of sodium and potassium), alkaline earth metal salts (for example those of calcium and magnesium), salts with organic bases such as triethanolamine, N-methyl-D-glucamine, piperidine, pyridine, piperazine, and morpholine, and salts with amino acids such as arginine and lysine.

Suitable solvates according to the invention include those formed with ethanol, water, saline, physiological buffer and glycol.

Unless otherwise specified, the term "alkyl" alone or in combination, means a straight-chain or branched-chain alkyl radical containing preferably from 1 to 6 carbon atoms, most preferably 1 to 4 carbon atoms. Examples of such radicals include, but are not limited to, methyl, ethyl, n-propyl, isopropyl, n-butyl, isobutyl, sec-butyl, tert-butyl, pentyl, iso-amyl, hexyl.

Unless otherwise specified, the term "alkoxy", alone or in combination, means an alkyl ether radical wherein the term alkyl is as defined above. Examples of suitable alkyl ether radicals include, but are not limited to, methoxy, ethoxy, n-propoxy, isopropoxy, n-butoxy, iso-butoxy, sec-butoxy, tert-butoxy.

"Alkyl amide" is an alkyl group as defined above linked to an amide, wherein an amide is the group —C(=O)—NR'R" wherein R' and R" are independently hydrogen or a hydrocarbon radical.

The term "halogen" or "halo-" means a substituent selected from fluorine, chlorine, bromine or iodine. "Haloalkyl" is an alkyl group as defined above substituted with one or more halogens.

The term "hydroxy" refers to the —OH radical.

In a preferred embodiment, Q is hydrogen.
X is preferably hydrogen, fluoro, bromo, iodo, hydroxy, $C_{1-4}$ alkyl, $C_{1-4}$ haloalkyl, $C_{1-4}$ alkoxy, or $C_{1-4}$ alkyl amide. X is most preferably hydrogen or $C_{1-4}$ alkoxy.
Y is preferably S or $SO_2$. Y is most preferably S.
R is preferably hydrogen, $C_{1-4}$ alkyl, or $C_{1-4}$ fluoroalkyl. R is most preferably $C_{1-4}$ fluoroalkyl.

In a preferred embodiment of Formula I:
X is hydrogen, fluoro, bromo, iodo, hydroxy, $C_{1-4}$ alkyl, $C_{1-4}$ haloalkyl, $C_{1-4}$ alkoxy, or $C_{1-4}$ alkyl amide;
Y is S or $SO_2$; and,
R is hydrogen, $C_{1-4}$ alkyl, or $C_{1-4}$ fluoroalkyl.

In a most preferred embodiment of Formula I:
Q is hydrogen;
X is $C_{1-4}$ alkoxy;
Y is S; and,
R is $C_{1-4}$ fluoroalkyl.

In an alternative preferred embodiment of Formula I:
Q is fluorine;
X is hydrogen;
Y is S; and,
R is $C_{1-4}$ fluoroalkyl.

Preferred radioisotopes suitable for in vivo imaging of the present invention are gamma-emitting radioactive halogens and positron-emitting radioactive non-metals.

Examples of gamma-emitting radioactive halogens suitable for use in the present invention are $^{123}I$, $^{131}I$ and $^{77}Br$. A preferred gamma-emitting radioactive halogen is $^{123}I$.

Examples of positron-emitting radioactive non-metal suitable for use in the present invention are $^{11}C$, $^{13}N$, $^{18}F$ and $^{124}I$. A preferred positron-emitting radioactive non-metal is $^{18}F$. $^{18}F$ is the most preferred radioisotope suitable for in vivo imaging of the present invention.

In a preferred embodiment, for the in vivo imaging agent of Formula I, X is $^{123}I$, $^{124}I$ or $^{131}I$, $^{18}F$ or $C_{1-4}$ [$^{18}F$]-fluoroalkyl.

In an alternative preferred embodiment, for the in vivo imaging agent of Formula I, R is $C_{1-4}$ [$^{18}F$]-fluoroalkyl.

In a further alternative preferred embodiment, for the in vivo imaging agent of Formula I the carbonyl carbon is $^{11}$C.

Non-limiting examples of some preferred in vivo imaging agents of the present invention are as follows:

1

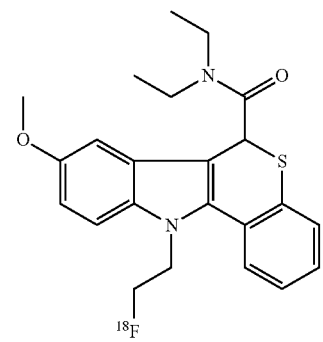

2

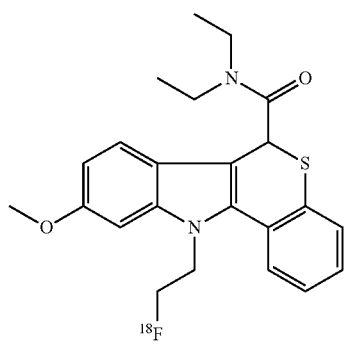

3

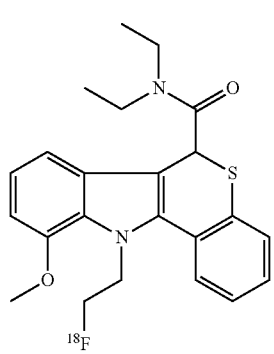

4

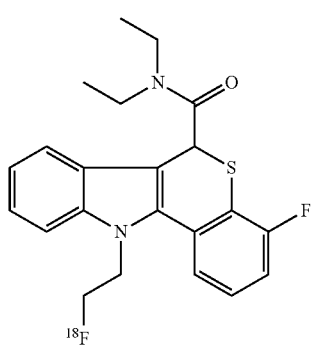

5

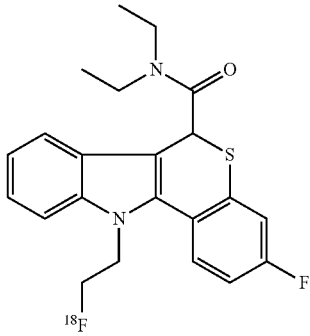

6

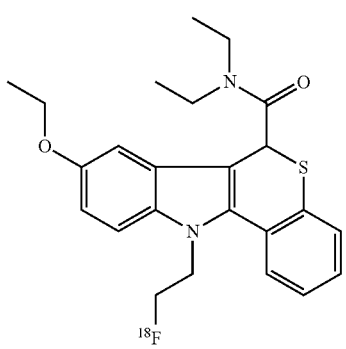

7

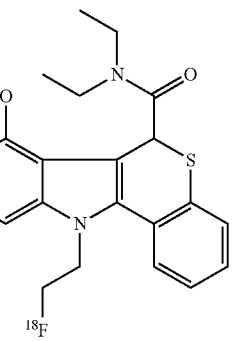

Out of the above in vivo imaging agents, imaging agent 2 is most preferred.

The synthetic methods used to obtain these in vivo imaging agents are described in the experimental section below. The potency of these non-radioactive versions of the in vivo imaging agents of the present invention was measured in an in vitro assay, as described in Example 10.

Examples 7-9 describe how to obtain the radiofluorinated in vivo imaging agents 1-7. The skilled person will know that when handling $^{18}$F the scale and the conditions used are different for safety and practical considerations. For a review of the production of $^{18}$F PET tracers, see chapters 1 and 2 of "Principles and Practice of Positron Emission Tomography" (2002 Lippincott Williams & Wilkins; Wahl and Buchanan, Eds.). The in vivo imaging agents were tested in an animal biodistribution model (Example 11), and their biodistribution compared to that of the prior art compound [$^{18}$F]FE-PBR (prepared according to Example 14 of WO 2007/057705):

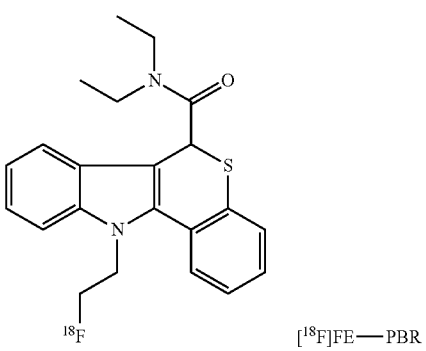

[18F]FE—PBR

Table 1 below provides data obtained in the in vitro affinity assay as well as in the in vivo biodistribution study. Non-radioactive analogues were tested in the in vitro affinity assay, and radiolabelled versions were evaluated in the biodistribution assay.

TABLE 1 in vitro affinity data and in vivo specific uptake data for in vivo imaging agents 1-7 of the present invention as compared with the prior art compound [18F]FE-PBR.

| In Vivo Imaging Agent | Ki nM | OB:Striatum @ 30 min |
|---|---|---|
| [18F]FE-PBR | 0.68 | 1.42 |
| 1 | 0.37 | 2.07 |
| 2 | 0.40 | 3.50 |
| 3 | 0.93 | 2.00 |
| 4 | 0.31 | 2.92 |
| 5 | 0.32 | 2.26 |
| 6 | 0.52 | 2.67 |
| 7 | 1.09 | 2.42 |

OB = olfactory bulb.

The data illustrate that the potency of non-radioactive versions of in vivo imaging agents 1-7 compares favourably with that of the prior art compound [18F]FE-PBR. In addition, the data show that in vivo imaging agents 1-7 of the invention are retained significantly more in the OB as compared with the striatum at 30 minutes post-injection compared with [18F]FE-PBR.] As it is known that PBR is highly expressed in the OB compared with other areas of the rat brain (see "Handbook of Substance Abuse" by Tarter, Ammerman and Ott; Springer 1998; 398-99) these data surprisingly demonstrate that in vivo imaging agents 1-7 have improved selectivity for PBR than the previously-exemplified in vivo imaging agent, [18F]FE-PBR.

In vivo imaging agent 1 was further analysed in an autoradiography model, as described in Example 12 below. Significantly higher levels of radioactivity were detected in the lesioned side of the facial nucleus (see FIGS. 1 and 2). Average intensity in the lesioned side was 7.75±0.95 as compared to 3.73±0.36 in the non-lesioned side. The ratio between the two sides was 8.23±2.36. As the lesion has a higher expression of PBR compared with normal, these data support the conclusion from the biodistribution data that in vivo imaging agent 1 has good selectivity for PBR.

The in vivo imaging agents of the present invention therefore have unexpectedly superior properties for in vivo imaging of PBR in comparison to known tetracyclic indole PBR-binding in vivo imaging agents.

Precursor Compound

In another aspect, the present invention provides a precursor compound of Formula II:

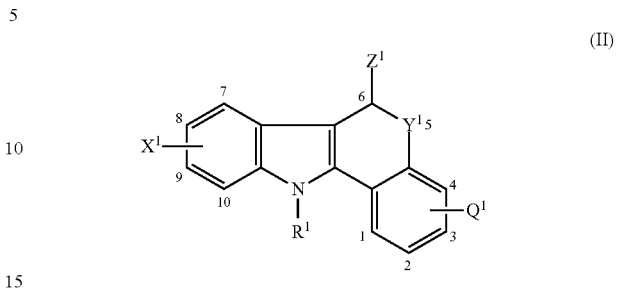

(II)

wherein one of $R^1$, $X^1$ or $Z^1$ comprises a chemical group that reacts with a suitable source of a radioisotope, where said radioisotope is as suitably and preferably defined herein, such that the in vivo imaging agent as suitably and preferably defined herein is formed upon reaction of said precursor compound with said suitable source of said radioisotope;

and wherein:

when $R^1$ does not comprise said chemical group it is as suitably and preferably defined herein for R of Formula I, and optionally further comprises a protecting group;

when $X^1$ does not comprise said chemical group it is as suitably and preferably defined herein for X of Formula I, and optionally further comprises a protecting group;

when $Z^1$ does not comprise said chemical group it is —C(=O)—N—(CH$_2$—CH$_3$)$_2$, and optionally further comprises a protecting group;

$Q^1$ is as suitably and preferably defined herein for Q of Formula I; and, $Y^1$ is as suitably and preferably defined herein for Y of Formula I, and optionally further comprises a protecting group.

A "precursor compound" comprises a derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity. The precursor compound may optionally comprise a protecting group for certain functional groups of the precursor compound.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tent-butyl; alkoxymethyl or alkoxyethyl; benzyl; acetyl; benzoyl; trityl (Trt) or trialkylsilyl such as tetrabutyldimethylsilyl. The use of further protecting groups are described in 'Protective Groups in Organic Synthesis', Theorodora W. Greene and Peter G. M. Wuts, (Third Edition, John Wiley & Sons, 1999).

The term "a suitable source of a radioisotope" means the radioisotope in a chemical form that is reactive with a substituent of the precursor compound such that the radioisotope becomes covalently attached to the precursor compound.

For each particular radioisotope presented in the following section, one or more suitable sources of the radioisotope are discussed. The person skilled in the art of in vivo imaging agents will be familiar with these and other sources of radioisotopes that are suitable for application in the present invention.

When the radioisotope of the in vivo imaging agent is $^{18}$F, the radiofluorine atom may form part of a fluoroalkyl or fluoroalkoxy group, since alkyl fluorides are resistant to in vivo metabolism. Alternatively, the radiofluorine atom may attach via a direct covalent bond to an aromatic ring such as a benzene ring.

Radiofluorination may be carried out via direct labelling using the reaction of $^{18}$F-fluoride with a suitable chemical group in the precursor compound having a good leaving group, such as an alkyl bromide, alkyl mesylate or alkyl tosylate.

$^{18}$F can also be introduced by O-alkylation of hydroxyl groups with $^{18}$F(CH$_2$)$_3$OMs or $^{18}$F(CH$_2$)$_3$Br.

For aryl systems, $^{18}$F-fluoride nucleophilic displacement from an aryl diazonium salt, aryl nitro compound or an aryl quaternary ammonium salt are suitable routes to aryl-$^{18}$F derivatives. Such a strategy is suitable for example to introduce $^{18}$F at positions 1-4 or 7-10 of Formula I.

Alternatively, labeling with $^{18}$F can be achieved by nucleophilic displacement of a leaving group from a derivative of Formula I. Suitable leaving groups include Cl, Br, I, tosylate (OTs), mesylate (OMs), and triflate (OTf). Such derivatives are precursor compounds for the preparation of in vivo imaging compounds of the invention.

Another strategy would be to have a suitable leaving group as defined above in place on an alkylamide group present on the precursor compound. In this way, the precursor compound may be labeled in one step by reaction with a suitable source of [$^{18}$F]-fluoride ion ($^{18}$F), which is normally obtained as an aqueous solution from the nuclear reaction $^{18}$O(p,n)$^{18}$F and is made reactive by the addition of a cationic counterion and the subsequent removal of water. For this method, the precursor compounds are normally selectively chemically protected so that radiofluorination takes place at a particular site on the compound. Suitable protecting groups are those already mentioned previously.

When the radioisotope is $^{18}$F, it is preferred that either X$^1$ or R$^1$ comprises either:

(i) an alkyl halide or an alkyl sulfonate (such as alkyl bromide, alkyl mesylate or alkyl tosylate) for neucleophilic substitution; or, (ii) hydroxyl (for introduction of $^{18}$F by O-alkylation of hydroxyl groups with e.g. $^{18}$F(CH$_2$)$_3$OMs or $^{18}$F(CH$_2$)$_3$Br).

A generic reaction scheme to arrive at certain $^{18}$F in vivo imaging agents of the invention is illustrated below:

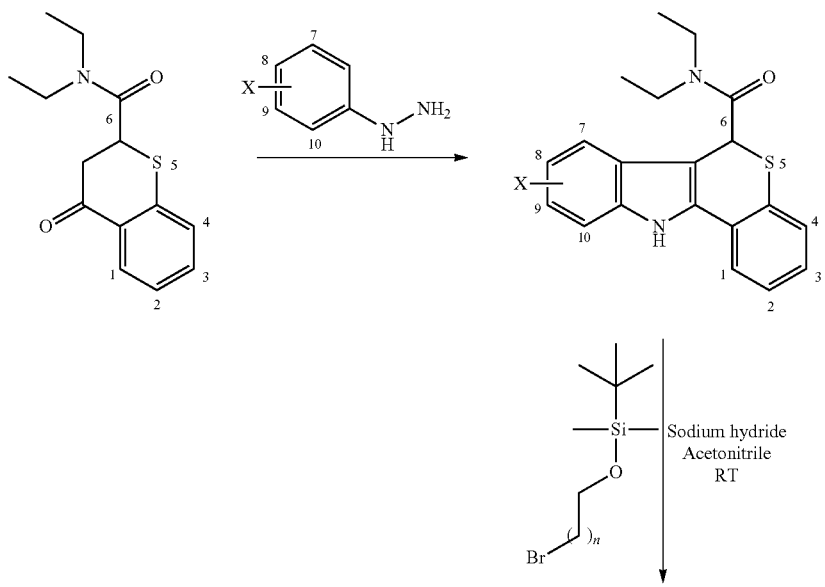

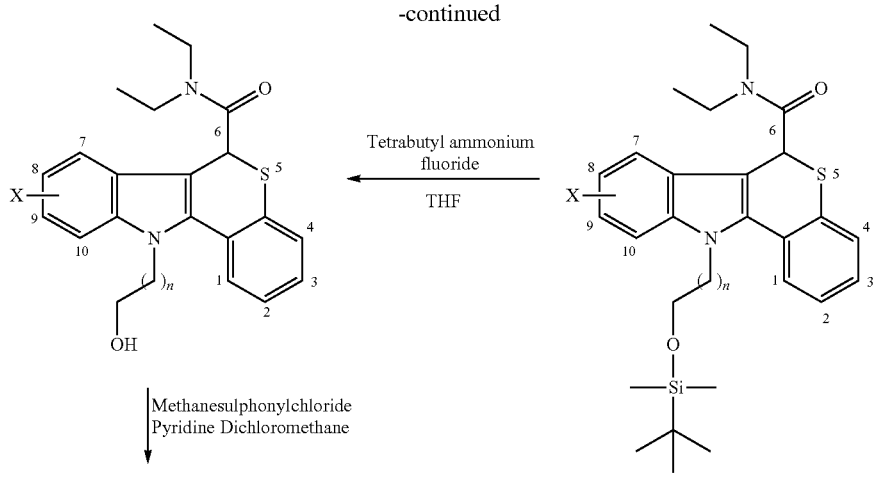
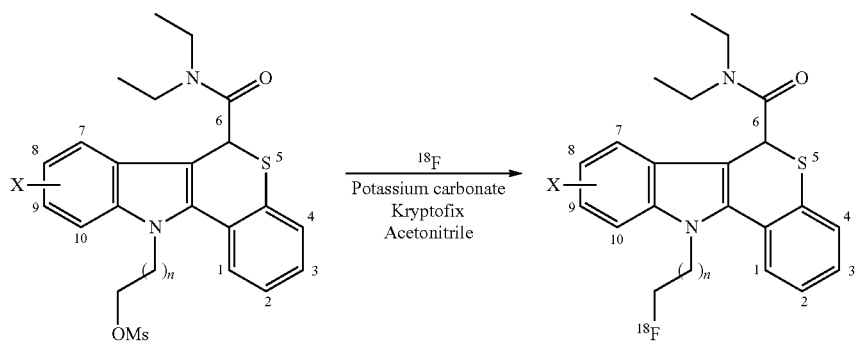
wherein X is as defined for Formula I, and n is between 0 and 5. RT stands for room temperature, and OMs stands for mesylate.
An alternative generic reaction scheme to arrive at certain $^{18}$F in vivo imaging agents of the invention is illustrated below:
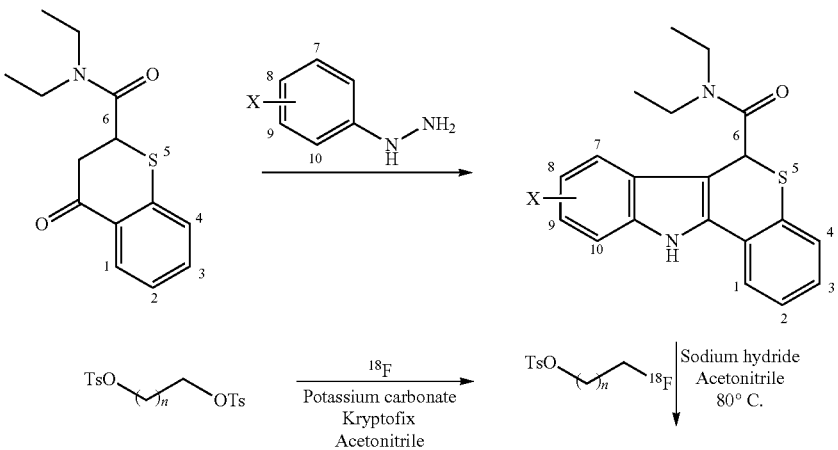

-continued

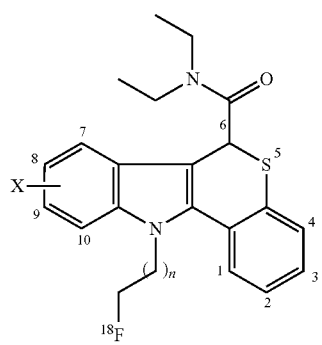

wherein X is as defined for Formula I, and n is between 0 and 5, and OTs stands for tosylate.

[11]C-labelled PET tracer compounds may be synthesised by reacting a precursor compound with $^{11}$C methyl iodide. As the half-life of $^{11}$C is only 20.4 minutes, it is important that the intermediate $^{11}$C methyl iodide has high specific activity and, consequently, that it is produced using a reaction process which is as rapid as possible. A thorough review of such $^{11}$C-labelling techniques may be found in Antoni et al "Aspects on the Synthesis of [11]C-Labelled Compounds" in Handbook of Radiopharmaceuticals, Ed. M. J. Welch and C. S. Redvanly (2003, John Wiley and Sons).

When the in vivo imaging agent of the present invention is labeled with $^{11}$C, the $^{11}$C is a carbonyl carbon. This therefore means that $^{11}$C can be present at the carbonyl carbon of Formula I, or alternatively at X when X is a $C_{1-6}$ alkyl amide.

A $^{11}$C-labelled in vivo imaging agent of Formula I may be obtained by employing the following reaction scheme:

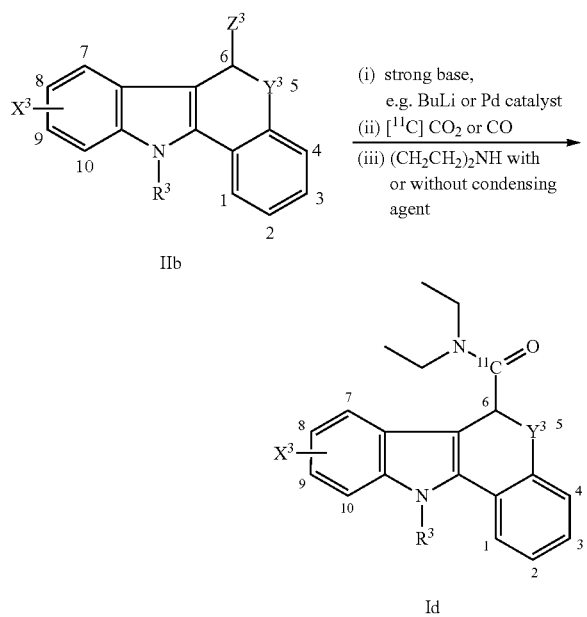

wherein $R^3$, $X^3$, and $Y^3$ of Formula IIb and Formula Id are as described for R, X, and Y of Formula I; and $Z^3$ is a substrate suitable for transition metal catalysts, e.g. hydrogen, halide, boronic acid, OTf, organotin.

Methods for the synthesis of $^{13}$N-labelled compounds are described by Clark and Aigbirhio ("Chemistry of Nitrogen-13 and Oxygen-15" in "Handbook of Radiopharmaceuticals"; 2003 Wiley: Welch and Redvanly, Eds.). For example, an in vivo imaging agent of Formula I may be obtained by nucleophilic substitution of a halogen in a suitable precursor compound with $^{13}$N-labelled diethyl amine to obtain the desired amide.

Where the imaging moiety is radioiodine, preferred precursor compounds are those which comprise a derivative which either undergoes electrophilic or nucleophilic iodination or undergoes condensation with a labelled aldehyde or ketone. Examples of the first category are:

(a) organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates);

(b) aromatic rings activated towards electrophilic iodination (e.g. phenols) and aromatic rings activated towards nucleophilic iodination (e.g. aryl iodonium salt aryl diazonium, aryl trialkylammonium salts or nitroaryl derivatives).

For radioiodination, the precursor compound preferably comprises: an aryl iodide or bromide (to permit radioiodine exchange); an activated precursor compound aryl ring (e.g. a phenol group); an organometallic precursor compound (e.g. trialkyltin, trialkylsilyl or organoboron compound); or an organic precursor compound such as triazenes or a good leaving group for nucleophilic substitution such as an iodonium salt. Precursor compounds and methods of introducing radioiodine into organic molecules are described by Bolton (J. Lab. Comp. Radiopharm. 2002; 45: 485-528). Precursor compounds and methods of introducing radioiodine into proteins are described by Wilbur (Bioconj. Chem. 1992; 3(6): 433-470). Suitable boronate ester organoboron compounds and their preparation are described by Kabalaka et al (Nucl. Med. Biol., 2002; 29: 841-843 and 2003; 30: 369-373). Suitable organotrifluoroborates and their preparation are described by Kabalaka et al (Nucl. Med. Biol., 2004; 31: 935-938). Preferred precursor compounds for radioiodination comprise an organometallic precursor compound, most preferably a trialkyltin.

Examples of aryl groups to which radioactive iodine can be attached are given below:

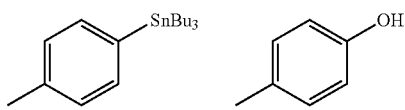

Both contain substituents which permit facile radioiodine substitution onto the aromatic ring. Alternative substituents containing radioactive iodine can be synthesised by direct iodination via radiohalogen exchange, e.g.

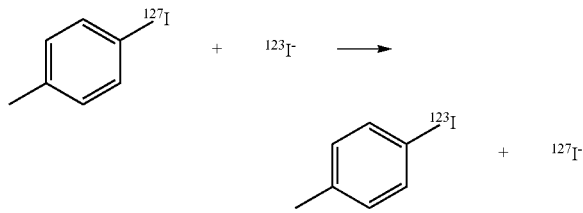

When the radioisotope is radioiodine, $X^1$ of Formula II, together with the aromatic group to which it is attached, forms:
  (i) an aromatic ring substituted with either an organometallic derivative or an organoboron compound;
  (ii) an aromatic ring activated towards electrophilic radioiodination (e.g. phenols); or,
  (iii) an aromatic ring activated towards nucleophilic radioiodination (e.g. aryl iodonium salt aryl diazonium, aryl trialkylammonium salts or nitroaryl derivatives).

These precursor compounds are easily converted into radioiodinated in vivo imaging agents of the invention by radioiodine substitution.

Radiobromination can be achieved by methods similar to those described above for radioiodination. Kabalka and Varma have reviewed various methods for the synthesis of radiohalogenated compounds, including radiobrominated compounds (Tetrahedron 1989; 45(21): 6601-21).

The precursor compound of the invention is ideally provided in sterile, apyrogenic form. The precursor compound can accordingly be used for the preparation of a pharmaceutical composition comprising the in vivo imaging agent together with a biocompatible carrier suitable for mammalian administration. The precursor compound is also suitable for inclusion as a component in a kit for the preparation of such a pharmaceutical composition.

In a preferred embodiment, the precursor compound is provided in solution and as part of a kit or of a cassette designed for use in an automated synthesis apparatus. These aspects are discussed in more detail below in relation to additional aspects of the invention.

In another preferred embodiment, the precursor compound is bound to a solid phase. The precursor compound is preferably supplied covalently attached to a solid support matrix. In this way, the desired product forms in solution, whereas starting materials and impurities remain bound to the solid phase. As an example of such a system, precursor compounds for solid phase electrophilic fluorination with $^{18}F$-fluoride are described in WO 03/002489, and precursor compounds for solid phase nucleophilic fluorination with $^{18}F$-fluoride are described in WO 03/002157.

Method for Preparation of In Vivo Imaging Agent

In a further aspect, the present invention provides a method for the preparation of an in vivo imaging agent of the invention, said method comprising:
  (i) providing a precursor compound of Formula II as defined above;
  (ii) providing a suitable source of said radioisotope as defined above;
  (iii) reacting the precursor compound of step (i) with the radioisotope of step (ii) to obtain an in vivo imaging agent of the invention.

In step (i), the precursor compound may be provided in solution in a kit or in a cassette suitable for use with an automated synthesis apparatus, or alternatively attached to a solid support, as described above in the description of the precursor compound. The kit and cassette form additional aspects of the invention and will be discussed in more detail below.

Suitable sources of radioisotope are as described above in relation to the precursor compound of the invention.

The step of "reacting" the precursor compound with the radioisotope involves bringing the two reactants together under reaction conditions suitable for formation of the desired in vivo imaging agent in as high a radiochemical yield (RCY) as possible. Particular synthetic routes for obtaining in vivo imaging agents of the present invention are presented in the experimental section below.

Kit for Preparation of In Vivo Imaging Agent

In a yet further aspect, the present invention provides a kit for the preparation of an in vivo imaging agent of the invention, said kit comprising a precursor compound of Formula II as described above, so that reaction with a sterile source of a radioisotope gives the desired in vivo imaging agent with the minimum number of manipulations. Such considerations are particularly important where the radioisotope has a relatively short half-life, and for ease of handling and hence reduced radiation dose for the radiopharmacist. The precursor compound is preferably present in the kit in lyophilized form, and the reaction medium for reconstitution of such kits is preferably a biocompatible carrier.

The "biocompatible carrier" is a fluid, especially a liquid, in which the in vivo imaging agent is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

In the kit of the invention, the precursor compound is preferably presented in a sealed container which permits maintenance of sterile integrity and/or radioactive safety, plus optionally an inert headspace gas (e.g. nitrogen or argon), whilst permitting addition and withdrawal of solutions by syringe. A preferred sealed container is a septum-sealed vial, wherein the gas-tight closure is crimped on with an overseal (typically of aluminium). Such sealed containers have the additional advantage that the closure can withstand vacuum if desired e.g. to change the headspace gas or degas solutions.

Preferred embodiments of the precursor compound when employed in the kit are as described herein.

The precursor compound for use in the kit may be employed under aseptic manufacture conditions to give the desired sterile, non-pyrogenic material. The precursor compound may alternatively be employed under non-sterile conditions, followed by terminal sterilisation using e.g. gamma-irradiation, autoclaving, dry heat or chemical treatment (e.g. with ethylene oxide). Preferably, the precursor compound is provided in sterile, non-pyrogenic form. Most preferably the sterile, non-pyrogenic precursor compound is provided in the sealed container as described above.

Preferably, all components of the kit are disposable to minimise the possibilities of contamination between runs and to ensure sterility and quality assurance.

In a preferred embodiment, the kit may comprise a cassette which can be plugged into a suitably adapted automated synthesiser, described in more detail below. Such a kit typically includes means for fluorinating with fluoride ion and may also comprise a column to remove unwanted fluoride ion. The reagents, solvents and other consumables required for the synthesis may also be included together with a data medium, such as a compact disc carrying software, which allows the automated synthesiser to be operated in a way to meet the end user's requirements for concentration, volumes, time of delivery etc.

[$^{18}$F]-radiotracers for PET imaging are now often conveniently prepared on an automated radiosynthesis apparatus. There are several commercially-available examples of such apparatus, including Tracerlab and Fastlab (GE Heathcare). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention therefore provides in another aspect a cassette for an automated synthesis apparatus comprising the precursor compound in a sealed container as described hereinbefore. The present invention also provides a cassette for the automated synthesis of an in vivo imaging agent as defined herein comprising:
  (i) a vessel containing a precursor compound as defined herein; and
  (ii) means for eluting the vessel with a suitable source of a radioisotope, said radioisotope as defined herein.

The cassette may additionally comprise:
  (iii) an ion-exchange cartridge for removal of excess radiolabel; and optionally,
  (iv) a cartridge for deprotection of the resultant radiolabelled product to form an in vivo imaging agent as defined herein.

Radiopharmaceutical Composition

In another further aspect, the present invention provides a "radiopharmaceutical composition", which is a composition comprising the in vivo imaging agent of the invention, together with a biocompatible carrier in a form suitable for mammalian administration. The biocompatible carrier is as defined above in relation to the kit of the invention.

The radiopharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). Where the in vivo imaging agent of the invention is provided as a radiopharmaceutical composition, the method for preparation of said in vivo imaging agent may further comprise the steps required to obtain a radiopharmaceutical composition, e.g. removal of organic solvent, addition of a biocompatible buffer and any optional further ingredients. For parenteral administration, steps to ensure that the radiopharmaceutical composition is sterile and apyrogenic also need to be taken.

In Vivo Imaging Method

In a yet further aspect, the present invention provides an in vivo imaging method for determining the distribution and/or the extent of PBR expression in a subject comprising:
  (i) administering to said subject an in vivo imaging agent as defined herein;
  (ii) allowing said in vivo imaging agent to bind to PBR in said subject;
  (iii) detecting by an in vivo imaging procedure signals emitted by the radioisotope of said in vivo imaging agent;
  (iv) generating an image representative of the location and/or amount of said signals; and,
  (v) determining the distribution and extent of PBR expression in said subject wherein said expression is directly correlated with said signals emitted by said in vivo imaging agent.

For the in vivo imaging method of the invention, the in vivo imaging agent is as defined earlier in the specification.

"Administering" the in vivo imaging agent is preferably carried out parenterally, and most preferably intravenously. The intravenous route represents the most efficient way to deliver the in vivo imaging agent throughout the body of the subject, and therefore also across the blood-brain barrier (BBB) and into contact with PBR expressed in said subject. The in vivo imaging agent of the invention is preferably administered as the pharmaceutical composition of the invention, as defined herein.

Following the administering step and preceding the detecting step, the in vivo imaging agent is allowed to bind to PBR. For example, when the subject is an intact mammal, the in vivo imaging agent will dynamically move through the mammal's body, coming into contact with various tissues therein. Once the in vivo imaging agent comes into contact with PBR, a specific interaction takes place such that clearance of the in vivo imaging agent from tissue with PBR takes longer than from tissue without, or with less PBR. A certain point in time will be reached when detection of in vivo imaging agent specifically bound to PBR is enabled as a result of the ratio between in vivo imaging agent bound to tissue with PBR versus that bound in tissue without, or with less PBR. An ideal such ratio is around 2:1.

The "detecting" step of the method of the invention involves detection of signals emitted by the radioisotope by means of a detector sensitive to said signals. This detection step can also be understood as the acquisition of signal data. Single-photon emission tomography (SPECT) and positron-emission tomography (PET) are the most suitable in vivo imaging procedures for use in the method of the invention. PET is a preferred in vivo imaging procedures for use in the method of the invention.

The "generating" step of the method of the invention is carried out by a computer which applies a reconstruction algorithm to the acquired signal data to yield a dataset. This dataset is then manipulated to generate images showing the location and/or amount of signals emitted by said radioisotope. The signals emitted directly correlate with the expression of PBR such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study PBR in healthy subjects, or in subjects known or suspected to have a pathological condition associated with abnormal expression of PBR (a "PBR condition"). Preferably, said method relates to the in vivo imaging of a subject known or suspected to have a PBR condition, and therefore has utility in a method for the diagnosis of said condition. Examples of such PBR conditions where in vivo imaging would be of use include neuropathologies such as Parkinson's disease, multiple sclerosis, Alzheimer's disease and Huntington's disease where neuroinflammation is present. Other PBR conditions that may be usefully imaged with the compounds of the invention include neuropathic pain, arthritis, asthma, atherosclerosis, as well as malignant diseases such as colorectal cancer and breast cancer. The in vivo imaging agents of the invention are particularly suited to in vivo imaging of the central nervous system (CNS) due to their good brain uptake.

In an alternative embodiment, the in vivo imaging method of the invention may be carried out repeatedly during the course of a treatment regimen for said subject, said regimen comprising administration of a drug to combat a PBR condition. For example, the in vivo imaging method of the invention can be carried out before, during and after treatment with a drug to combat a PBR condition. In this way, the effect of said treatment can be monitored over time. Preferably for this embodiment, the in vivo imaging procedure is PET. PET has excellent sensitivity and resolution, so that even relatively small changes in a lesion can be observed over time, which is advantageous for treatment monitoring. PET scanners routinely measure radioactivity concentrations in the picomolar range. Micro-PET scanners now approach a spatial resolution of about 1 mm, and clinical scanners about 4-5 mm.

In a further aspect, the present invention provides a method for diagnosis of a PBR condition. The method of diagnosis of the invention comprises the method of in vivo imaging as defined above, together with the further step (vi) of attributing the distribution and extent of PBR expression to a particular clinical picture, i.e. the deductive medical decision phase.

In another aspect, the present invention provides the in vivo imaging agent as defined herein for use in the method of diagnosis as defined herein.

In a yet further aspect, the present invention provides the in vivo imaging agent as defined herein for use in the manufacture of a radiopharmaceutical composition as defined herein for use in the method of diagnosis as defined herein.

Brief Description of the Examples

All reagents were obtained from Sigma Aldrich.

Examples 1-6 describe the synthesis of non-radioactive versions of various in vivo imaging agents of the invention.

Examples 7-9 describe how to obtain $^{18}$F-labelled in vivo imaging agents of the invention.

Example 10 describes the in vitro potency assay used to measure PBR affinity of the imaging agents of the invention.

Example 11 describes how the animal biodistribution studies were carried out.

Example 12 describes the facial nerve axotomy animal model and its use in an autoradiography study.

LIST OF ABBREVIATIONS USED IN THE EXAMPLES

DCM dichloromethane
DMF dimethylformamide
DMSO dimethyl sulfoxide
EtOAc ethyl acetate
FNA: facial nerve axotomy
g gram(s)
h hour(s)
HRMS high resolution mass spectrometry
K222 Kryptofix 2.2.2
M molarity=moles of solute/litre of solution
MHz mega hertz
ml millilitre(s)
mmol milimole(s)
N normality=number of equivalents/1 L of solution
NMR nuclear magnetic resonance
PBR peripheral benzodiazepine receptor
RT room temperature

EXAMPLES

Example 1

Preparation of (+-)-11-(2-fluoroethyl)-8-methoxy-6,11-dihydro-5-thia-11-aza-benzo[a]fluorene-6-carboxylic acid diethyl amide (non-radioactive imaging agent 1)

Example 1(i). (+-)-4-Oxo-thiochroman-2-carboxylic acid diethyl amide

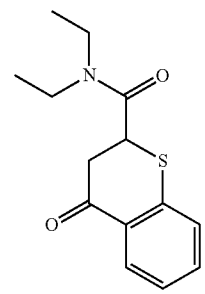 [SMILES: CCN(CC)C(=O)C1CC(=O)c2ccccc2S1]

(+-)-4-Oxo-thiochroman-2-carboxylic acid (10.4 g, 50 mmol), prepared as described in T. Okubo et al (Bioorg. Med. Chem. 2004; 12: 3569-3580), in dry DCM (100 ml) was stirred under an atmosphere of nitrogen at room temperature with oxalyl chloride (12.6 g, 100 mmole) and one drop of DMF for 18 h. The reaction was then evaporated in vacuo to a gum and then redissolved in DCM (100 ml), cooled to 0° C. on an ice bath, stirred and treated dropwise with diethylamine (8.03 g, 110 mmol) in DCM (20 ml) over a period of 1 h. The reaction was allowed to warm to room temperature over 1 h and 10% aqueous potassium carbonate solution (100 ml) was added and the reaction mixture vigorously stirred. The DCM solution was separated. The aqueous solution was extracted with two further batches of DCM (100 ml) and the combined extracts were dried over magnesium sulphate. The DCM solution was concentrated in vacuo to give a dark green oil that crystallized on standing. The crystalline solid was triturated with diethyl ether (50 ml) and filtered to give the title compound (8.57 g, 65%) as a pale green solid.

¹H NMR (300 MHz, CDCl₃) δ 1.06 (t, J=7.1 Hz, 3H), 1.23 (t, J=7.1 Hz, 3H), 3.0-3.5 (m, 6H), 4.25 (m, 1H), 7.15-7.21 (m, 2H), 7.32-7.39 (m, 1H), 8.10-8.14 (m, 1H).
¹³C NMR (75 MHz, CDCl₃) δ 12.9, 14.8, 40.1, 40.7, 42.3, 42.5, 125.8, 127.2, 128.7, 130.8, 133.4, 137.9, 167.9, 193.1

Example 1(ii): (+-)-8-methoxy-6,11-dihydro-5-thia-11-aza-benzo[a]fluorene-6-carboxylic acid diethyl amide

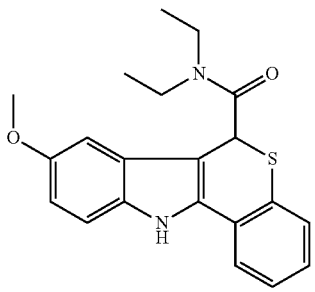 [SMILES: CCN(CC)C(=O)C1Sc2ccccc2-c2[nH]c3ccc(OC)cc3c21]

To a solution of (+-)-4-Oxo-thiochroman-2-carboxylic acid diethyl amide (1.32 g, 5.0 mmol, Example 1(i)) and 4-methoxyphenyl hydrazine hydrochloride (0.87 g, 5.0 mmol) in ethanol (10 ml) was added concentrated sulphuric acid (0.73 ml, 1.35 g, 13.8 mmol) under nitrogen. The reaction mixture was heated under reflux for 24 h. After cooling, the reaction mixture was filtered, the solid washed with ethanol, dried in vacuo (45° C.) to give the title compound (1.05 g, 57%) as a pale yellow solid.

¹H NMR (300 MHz, DMSO-d₆) δ 0.97 (t, J=6.8 Hz, 3H), 1.28 (t, J=6.8 Hz, 3H), 3.25 (m, 2H), 3.60 (m, 2H), 3.74 (s, 3H), 5.59 (s, 1H), 6.80 (m, 2H), 7.10-7.35 (m, 4H), 7.75 (d, J=7.3 Hz, 1H, NH).
¹³C NMR (75 MHz, DMSO-d₆) δ 10.5, 12.7, 32.7, 37.9, 39.5, 53.0, 97.6, 103.3, 109.87, 109.92, 120.3, 123.5, 123.8, 124.3, 124.7, 124.9, 127.8, 129.4, 131.8, 151.3, 166.2
m/z (ES⁺) 367.1 (M⁺H).

Example 1(iii). (+-)-11-(2-fluoroethyl)-8-methoxy-6,11-dihydro-5-thia-11-aza-benzo[a]fluorene-6-carboxylic acid diethyl amide

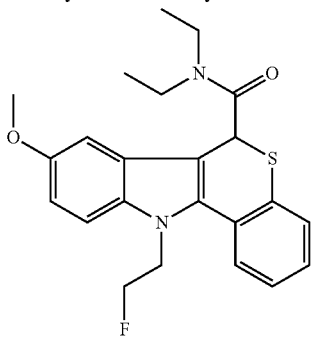

To a solution of (+-)-8-methoxy-6,11-dihydro-5-thia-11-aza-benzo[a]fluorene-6-carboxylic acid diethyl amide (150 mg, 0.41 mmol; Example 1(ii)) in anhydrous DMF (4 ml) was added 2-fluoroethyl tosylate (166 mg, 0.82 mmol), prepared as described in L. Cronin et al (J. Org. Chem. 2004; 69: 5934-5946) followed by sodium hydride 60% dispersion in mineral oil (34 mg, 0.82 mmol) under nitrogen. The reaction mixture was heated at 80° C. for 1 h. After cooling, the solvents were removed in vacuo, the residue quenched with water (30 ml), extracted with DCM (2×30 ml), dried (MgSO₄) and solvents removed in vacuo. The residue was purified by column chromatography on silica, eluting with 5-10% EtOAc/CH₂Cl₂. The crude solid was quenched with ether/pet.spirit, filtered, dried in vacuo (45° C.) to give the title compound (77 mg, 46%) as a pale brown solid.

¹H NMR (300 MHz, CDCl₃) δ 1.12 (t, J=7.0 Hz, 3H), 1.36 (t, J=7.0 Hz, 3H), 3.25-3.70 (m, 4H), 3.83 (s, 3H), 4.45-4.70 (m, 2H), 4.80 (t, J=5.2 Hz, 1H), 4.96 (t, J=5.2 Hz, 1H), 5.09 (s, 1H), 6.84-6.93 (m, 2H), 7.13-7.32 (m, 3H), 7.46 (m, 1H), 7.58 (d, J=8.0 Hz, 1H).
¹³C NMR (75 MHz, CDCl₃) δ 12.9, 14.9, 37.3, 41.1, 42.5, 45.5, 45.8, 55.9, 81.2, 83.5, 100.4, 110.1, 111.09, 111.12, 112.8, 124.31, 124.35, 125.2, 126.5, 127.1, 127.6, 128.8, 132.2, 134.4, 137.0, 154.8, 168.0
¹⁹F NMR (282 MHz, CDCl₃) δ -219.4, -219.5, -219.6, -219.65, -219.73, -219.8, -219.9
m/z (ES) 413.1 (M⁺H).

Example 2

Preparation of (+-)-11-(2-fluoroethyl)-10-methoxy-6,11-dihydro-5-thia-11-aza-benzo[a]fluorene-6-carboxylic acid diethyl amide (non-radioactive imaging agent 3)

Example 2(i): (+-)-10-methoxy-6,11-dihydro-5-thia-11-aza-benzo[a]fluorene-6-carboxylic acid diethyl amide

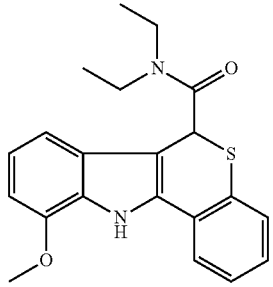 [SMILES: CCN(CC)C(=O)C1Sc2ccccc2-c2[nH]c3c(OC)cccc3c21]

This compound was prepared as described for Example 1(ii) except that 2-methoxyphenyl hydrazine hydrochloride was used instead of 4-methoxyphenyl hydrazine hydrochloride. The compound was obtained in 40% yield.
m/z (ES⁺) 367.0 (M⁺H).

Example 2 (ii): (+-)-11-2-fluoroethyl)-10-methoxy-6,11-dihydro-5-thia-11-aza-benzo[a]fluorene-6-carboxylic acid diethyl amide

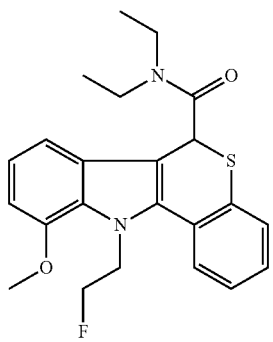 [SMILES: CCN(CC)C(=O)C1Sc2ccccc2-c2c1c1cccc(OC)c1n2CCF]

This compound was prepared as described for Example 1(iii) except that (+-)-10-methoxy-6,11-dihydro-5-thia-11-aza-benzo[a]fluorene-6-carboxylic acid diethyl amide (Example 2(i)) was used instead of (+-)-8-methoxy-6,11-dihydro-5-thia-11-aza-benzo[a]fluorene-6-carboxylic acid diethyl amide. After recrystallisation (ether), was obtained in 10% yield as a white solid.

$^1$H NMR (300 MHz, CDCl$_3$) δ 1.09 (t, J=7.0 Hz, 3H), 1.35 (t, J=7.0 Hz, 3H), 3.25-3.67 (m, 4H), 3.95 (s, 3H), 4.70-4.96 (m, 4H), 5.04 (s, 1H), 6.67 (m, 1H), 7.04 (m, 2H), 7.16 (m, 1H), 7.29 (m, 1H), 7.45 (m, 1H), 7.77 (m, 1H).

m/z (ES$^+$) 413.1 (M$^+$H).

Example 3

Preparation of (+-)-4-fluoro-11-(2-fluoroethyl)-6,11-dihydro-5-thia-11-aza-benzo[a]fluorene-6-carboxylic acid diethyl amide (non-radioactive imaging agent 4)

Example 3(i): (+-)-8-Fluoro-4-oxo-thiochromana-2-carboxlic acid

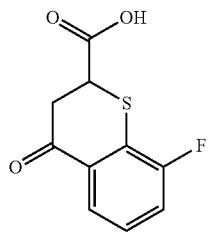 [SMILES: O=C1CC(C(=O)O)Sc2c(F)cccc21]

In a round bottom flask 2-fluorothiophenol (5.0 g, 39.0 mmol, 4.16 mL) and furan-2,5-dione (3.82 g, 39.0 mmol) in toluene (12 mL) were stirred at 50° C. for 40 minutes. Triethylamine (100 µl) in toluene (5 mL) was then added over 10 minutes ensuring the reaction temperature did not increase over 60° C. The reaction was then heated at 70° C. for 20 minutes. The reaction was then concentrated under high vacuum to obtain the crude product as an oil. This material was dissolved in DCM (75 mL), cooled on an ice bath and treated with aluminium trichloride (7.78 g, 58.5 mmol) in small portions so as to keep the temperature below 10° C. The reaction was warmed to RT and there was a vigorous evolution of hydrogen chloride gas and the reaction became very viscous and turned red. After stirring at RT for 1.5 hours the reaction mixture was then diluted with DCM (50 mL) to make it less viscous and slowly poured into vigorously stirred concentrated hydrochloric acid (30 mL) and ice (30 g) in a 2 L conical flask. The reaction was vigorously stirred and diluted with a further portion of DCM (500 mL) and isopropyl alcohol (50 mL) to dissolve any solid that had crystallized out. The DCM layer was separated, dried over magnesium sulfate and concentrated in vacuum to give a brown solid. The crude solid was purified by triturated with diethyl ether and a cream solid was collected by filtration to give 2.5 g (28%) of 8-Fluoro-4-oxo-thiochromana-2-carboxlic acid. $^1$H NMR (300 MHz; DMSO-d$_3$): δ 3.04-3.20 (2H, m, 3-H), 4.51 (1H, dd, J=4 and 6 Hz, 2-H), 7.26-7.34 (1H, m, 6-H), 7.45-7.52 (1H, in, 7-H), 7.82 (1H, dd, J=1 and 8 Hz, 5H). $^{13}$C NMR (75 MHz; DMSO-d$_3$): δ 40.5, 40.7, 119.8, 120.1, 123.88, 123.92, 126.0, 126.1, 131.9, 156.1, 159.2, 171.5, 191.2, 191.3.

Example 3(ii): (+-)-8-Fluoro-4-oxo-thiochroman-2-carboxylic acid diethylamide

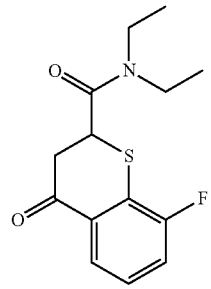 [SMILES: CCN(CC)C(=O)C1CC(=O)c2cccc(F)c2S1]

8-Fluoro-4-oxo-thiochromana-2-carboxlic acid (2.5 g, 11.1 mmol) in dry DCM (50 ml) was stirred under an atmosphere of nitrogen at room temperature with oxalyl chloride (2.81 g, 22.1 mmo, 1.93 mL) and one drop of DMF to catalyse the reaction for 18 h. The acid was initially insoluble but dissolved as it reacted to give a orange clear solution after 2 hours and then turned black after 24 h. The reaction was then evaporated in vacuum to a gum to remove excess oxalyl chloride and $^1$H and $^{13}$C NMR run in CDCl$_3$ to confirm complete reaction. The reaction was then redissolved in DCM (50 ml) cooled to 0° C. on an ice bath stirred and treated dropwise with diethylamine (1.66 g, 22.7 mmol, 2.05 mL) in DCM (20 ml) over a period of 1 h. The reaction was allowed to warm to room temperature over a period of 1 h. The reaction was then quenched by the addition of 5% potassium carbonate solution (100 ml) and the reaction mixture stirred vigorously. The DCM solution was separated and dried over magnesium sulphate. Two further batches of DCM (100 ml) were shaken with the aqueous solution, and then separated and dried over magnesium sulphate. The combined DCM solutions were concentrated in vacuum to give a brown solid. The crude solid was purified by hot recrystallisation from ethyl acetate and petrol to afford 1.73 g (56%) of 8-Fluoro-4-oxo-thiochroman-2-carboxylic acid diethylamide as yellow crystals. $^1$H NMR (300 MHz; CDCl$_3$): δ 1.07 (3H, t, J=7 Hz, N(CH$_2$C$\underline{H}_3$)$_2$), 1.26 (3H, t, J=7 Hz, N(CH$_2$C$\underline{H}_3$)$_2$), 3.02-3.55 (6H, m, 2-H and N(C$\underline{H}_2$CH$_3$)$_2$), 4.24-4.27 (1H, m, 2-H), 7.15-7.19 (2H, m, 6-H and 7-H), 7.93-7.97 (1H, m, 5-H).

LC-MS: m/z calcd for C$_{14}$H$_{16}$FNO$_2$S 281.1; found, 282.0 (M+H)+

Example 3(iii): (+-)-4-Fluoro-6,11-dihydro-5-thia-11azabenzo[a]fluorene-6-carboxylic acid diethylamide

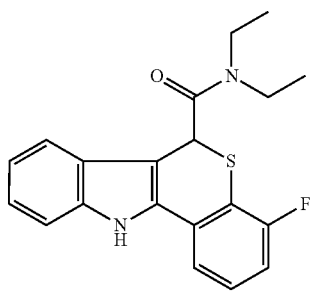 [SMILES: CCN(CC)C(=O)C1Sc2c(F)cccc2-c2[nH]c3ccccc3c21]

8-Fluoro-4-oxo-thiochromana-2-carboxylic acid diethylamide (1.7 g, 6.0 mmol) and phenyl hydrazine 0.65 g, 6.0 mmol, 0.6 mL) in ethanol (10 mL) and sulphuric acid (conc., 0.8 mL) were stirred at reflux for overnight. After cooling the reaction was filtered and the white solid was collected to afford 1.4 g (80%) of crude material (90% pure). The crude solid (500 mg) was purified by hot re-crystallisation from ethanol to afford 277 mg (13%) of 4-Fluoro-6,11-dihydro-5-thia-11-aza-benzo[a]fluorene-6-carboxylic acid diethylamide as white crystals. The structure was confirmed by $^1$H NMR (300 MHz; DMSO-d$_6$): δ 0.96 (3H, t, J=7 Hz, N(CH$_2$CH$_3$)$_2$), 1.30 (3H, t, J=9 Hz, N(CH$_2$CH$_3$)$_2$), 3.19-3.25 (2H, m, N(CH$_2$CH$_3$)$_2$), 3.56-3.66 (2H, m, N(CH$_2$CH$_3$)$_2$), 5.76 (1H, s, 6-H), 7.02-7.45 (6H, m, ArH), 7.65 (1H, dd, J=1 and 6 Hz, ArH), 11.8 (1H, s, NH).

LC-MS: m/z calcd for C$_{20}$H$_{19}$FN$_2$OS 354.2; found, 355.0 (M+H)+

Example 3(iv): (+)-4-fluoro-11-(2-fluoroethy) -6,11-dihydro-5-thia-11-aza-benzo[a]fluorene-6-carboxylic acid diethyl amide

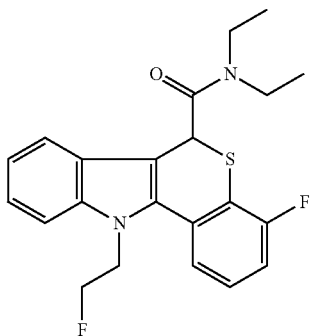 [SMILES: CCN(CC)C(=O)C1Sc2c(F)cccc2-c2c1c1ccccc1n2CCF]

(+-)-4-Fluoro-6,11-dihydro-5-thia-11azabenzo[a]fluorene-6-carboxylic acid diethylamide (0.10 g, 0.28 mmol) was dissolved in dry DMF (6 mL) at room temperature under nitrogen. Fluoroethyl tosylate (0.12 g, 0.12 mmol) was added and then NaH (0.02 g, 0.56 mmol, 60% in oil). The reaction was heated to 80° C. for 1 hour. The solvent was removed under reduced pressure and the residue was dissolved in DCM and washed with water. The organics were dried over MgSO$_4$, filtered and evaporated to dryness. The crude material was crystallized from methanol to afford 34.4 mg (30%) of 4-Fluoro-11-(2-fluoro-ethyl)-6,11-dihydro-5-thia-11-aza-benzo[a]fluorene-6-carboxylic acid diethylamide as a white solid. $^1$H NMR (300 MHz, DMSO-d$_6$) δ 0.94 (3H, t, J=7 Hz, N(CH$_2$CH$_3$)$_2$), 1.29 (3H, t, J=7 Hz, N(CH$_2$CH$_3$)$_2$), 3.14-3.26 (2H, m, N(CH$_2$CH$_3$)$_2$), 3.55-3.65 (2H, m, N(CH$_2$CH$_3$)$_2$), 4.65-4.95 (4H, m, NCH$_2$CH$_2$F), 5.62 (1H, s, 6-H), 7.12-7.37 (4H, m, ArH), 7.48 (1H, d, J=9 Hz, ArH), 7.61-7.68 (2H, m, ArH).

LC-MS: m/z calcd for C$_{22}$H$_{22}$F$_2$N$_2$OS 401.1; found, 401.1 (M+H)+.

Example 4

Preparation of (+-)3-fluoro-11-(2-fluoroethyl)-6,11-dihydro-5-thia-11-aza-benzo[a]fluorene-6-carboxylic acid diethyl amide (non-radioactive imaging agent 5)

Example 4(i): (+-)-7-Fluoro-4-oxo-thiochromana-2-carboxlic acid

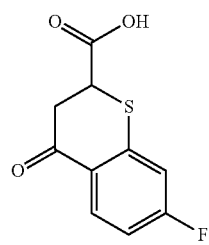 [SMILES: O=C1CC(C(=O)O)Sc2cc(F)ccc21]

In a round bottom flask 3-Fluorothiophenol (10.0 g, 71.3 mmol, 8.85 mL) and furan-2,5-dione dione (7.0 g, 71.3 mmol) in toluene (12 mL) were stirred at 50° C. for 40 minutes. Triethylamine (26 μl) in toluene (1 mL) was then added over 10 minutes insuring the reaction temperature did not increase over 60° C. The reaction was then heated at 70° C. for 20 minutes. The reaction was then concentrated under high vacuum to obtain the crude product as an oil. This material was dissolved in DCM (75 mL), cooled on an ice bath and treated with aluminium trichloride (7.78 g, 58.5 mmol) in small portions so as to keep the temperature below 10° C. The reaction was warmed to RT and there was a vigorous evolution of hydrogen chloride gas and the reaction became very viscous and turned red. After stirring at room temperature for 1.5 hours the reaction mixture was then diluted with DCM (50 mL) to make it less viscous and slowly poured into vigorously stirred concentrated hydrochloric acid (30 mL) and ice (30 g) in a 2 L conical flask. The reaction was vigorously stirred and diluted with a further portion of DCM (500 mL) and isopropyl alcohol (50 mL) to dissolve any solid that had crystallized out. The DCM layer was separated, dried over magnesium sulfate and concentrated in vacuum to give a brown solid. The solid was triturated with diethyl ether and then filtered to give 4.2 g (48%) of 7-Fluoro-4-oxo-thiochroman-2-carboxylic acid as a cream solid. $^1$H NMR (300 MHz, DMSO-d$_3$): δ 3.00-3.16 (2H, m, 3-H), 4.44 (1H, dd, J=5 and 10 Hz, 2-H), 7.08 (1H, td, J$_1$=3 and 9 Hz, 6-H), 7.30 (1H, dd, J=5 and 10 Hz, ArH), 8.01 (1H, dd, J$_1$=5 and 10 Hz, ArH). $^{13}$C NMR (75 MHz; DMSO-d$_3$): δ 38.0, 39.6, 111.1, 111.3, 111.5, 111.8, 125.0, 125.1, 129.0, 129.2, 139.6, 139.7, 160.9, 164.3, 169.5, 188.9.

Example 4(ii). (+-)-7-Fluoro-4-oxo-thiochromana-2-carboxlic acid diethylamide

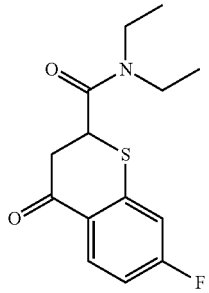 [SMILES: CCN(CC)C(=O)C1CC(=O)c2ccc(F)cc2S1]

7-Fluoro-4-oxo-thiochromana-2-carboxlic acid (4 g, 17.7 mmol) in dry DCM (50 ml) was stirred under an atmosphere of nitrogen at room temperature with oxalyl chloride (4.49 g, 35.4 mmol, 3.1 mL) and one drop of DMF to catalyse the reaction for 18 h. The acid was initially insoluble but dissolved as it reacted to give a orange clear solution after 2 hours and then turned black after 18 h. The reaction was then evaporated in vacuum to a gum to remove excess oxalyl chloride and $^1$H and $^{13}$C NMR run in CDCl$_3$ to confirm complete reaction. The reaction was then redissolved in DCM (50 ml) cooled to 0° C. on an ice bath stirred and treated dropwise with diethylamine in DCM (10 ml) over a period of 1 h. The reaction was allowed to warm to room temperature over a period of 1 h. The reaction was then quenched by the addition of 5% potassium carbonate solution (50 ml) and the reaction mixture stirred vigorously. The DCM solution was separated and dried over magnesium sulphate. Two further batches of DCM (50 ml) were shaken with the aqueous solution, and then separated and dried over magnesium sulphate. The combined DCM solutions were concentrated in vacuum to give a brown solid, which crystallised on standing to afford 5.03 g (quant) of 7-fluoro-4-oxo-thiochroman-2-carboxylic acid diethylamide. The structure was confirmed by $^1$H NMR (300 MHz; CDCl$_3$): δ 1.07 (3H, t, J=7 Hz, N(CH$_2$CH$_3$)$_2$), 1.24 (3H, t, J=7 Hz, N(CH$_2$CH$_3$)$_2$), 2.99-3.50 (6H, m, 2-H and N(CH$_2$CH$_3$)$_2$), 4.24-4.27 (1H, m, 2-H), 6.83-6.94 (2H, m, 6-H and 8-H), 8.15 (1H, dd, J=6 and 9 Hz, 5-H).

LC-MS: m/z calcd for C$_{14}$H$_{16}$FNO$_2$S 281.1; found, 282.0 (M+H)+

Example 4(iii): (+-)-3-Fluoro-6,11-dihydro-5-thia-11-aza-benzo[a]fluorene-6-carboxylic acid diethylamide

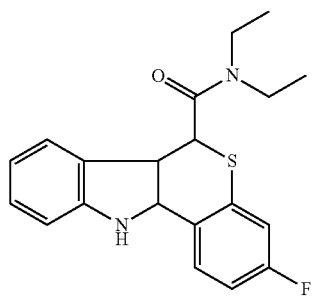 [SMILES: CCN(CC)C(=O)C1Sc2cc(F)ccc2C2Nc3ccccc3C12]

7-Fluoro-4-oxo-thiochromana-2-carboxylic acid diethylamide (2.5 g, 8.9 mmol) and phenyl hydrazine 0.96 g, 8.9 mmol, 0.9 mL) in ethanol (10 mL) and sulphuric acid (conc., 1.2 mL) were stirred at reflux for overnight. The crude solid was purified by hot re-crystallisation from ethanol to afford 1.49 g (47%) of 3-Fluoro-6,11-dihydro-5-thia-11-aza-benzo[a]fluorene-6-carboxylic acid diethylamide as white crystals. $^1$H NMR (300 MHz; DMSO-d$_6$): δ 0.96 (3H, t, J=6 Hz, N(CH$_2$CH$_3$)$_2$), 1.29 (3H, t, J=6 Hz, N(CH$_2$CH$_3$)$_2$), 3.19-3.25 (2H, m, N(CH$_2$CH$_3$)$_2$), 3.55-3.61 (2H, m, N(CH$_2$CH$_3$)$_2$), 5.66 (1H, s, 6-H), 7.03 (1H, td, J=1 and 8 Hz, ArH), 7.09-7.18 (2H, m, ArH), 7.25 (1H, dd, J=3 and 9 Hz, ArH), 7.35 (1H, d, J=8 Hz, ArH), 7.41 (1H, d, J=8 Hz, ArH), 7.81 (1H, dd, J=6 and 9 Hz, ArH), 11.68(1H, s, NH).

LC-MS: m/z calcd for C$_{20}$H$_{19}$FN$_2$OS 352.1; found, 353.2 (M+H)+.

Example 4(iv). (+-) 3-Fluoro-11-(2-fluoro-ethyl)-6,11-dihydro-5-thia-11-aza-benzo[a]fluorene-6-carboxylic acid diethylamide

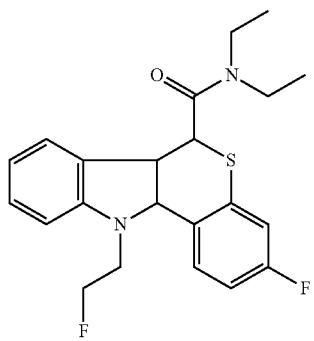 [SMILES: CCN(CC)C(=O)C1Sc2cc(F)ccc2C2C1c1ccccc1N2CCF]

3-Fluoro-6,11-dihydro-5-thia-11-aza-benzo[a]fluorene-6-carboxylic acid diethylamide (0.20 g, 0.56 mmol) was dissolved in dry DMF (6 mL) at room temperature under nitrogen. Fluoroethyl tosylate (0.25 g, 1.13 mmol) was added and then NaH (0.05 g, 1.13 mmol, 60% in oil). The reaction was heated to 80° C. for 1 hour. The solvent was removed under reduced pressure and the residue was dissolved in DCM and washed with water. The organics were dried over MgSO$_4$, filtered and evaporated to dryness. The crude material was purified by semi preparative HPLC eluting with water (A) and acetonitrile (B) (Gemini 5u, C18, 110A, 150×21 mm, 5-95% B over 20 min, 21 mL/min) to afford 79.9 mg (35%) of 3-Fluoro-11-(2-fluoro-ethyl)-6,11-dihydro-5-thia-11-aza-benzo[a]fluorene-6-carboxylic acid diethylamide as a white solid. $^1$H NMR (300 MHz, DMSO-d$_6$) δ 0.95 (3H, t, J=9 Hz, N(CH$_2$CH$_3$)$_2$), 1.88 (3H, t, J=9 Hz, N(CH$_2$CH$_3$)$_2$), 3.14-3.26 (2H, m, N(CH$_2$CH$_3$)$_2$), 3.51-3.67 (2H, m, N(CH$_2$CH$_3$)$_2$), 4.58-4.97 (4H, m, NCH$_2$CH$_2$F), 5.53 (1H, s, 6-H), 7.12-7.27 (3H, m, ArH), 7.38-4.47 (2H, m, ArH), 7.61 (1H, d, J=9 Hz, ArH), 7.80-7.86 (1H, m, ArH).

LC-MS: m/z calcd for C$_{22}$H$_{22}$F$_2$N$_2$OS 401.1; found, 401.1 (M+H)+.

Example 5

Preparation of (+−)8-ethoxy-11-(2-fluoroethyl)-6,11-dihydro-5-thia-11-aza-benzo[a]fluorene-6-carboxylic acid diethyl amide (non-radioactive imaging agent 6)

Example 5(i): (+−) 11-[2-(tertbutyl-dimethyl-silanyloxy)]ethyl]-8-methoxy-6,11-dihydro-5-thia-11-aza-benzo[a]fluorene-6-carboxylic acid diethylamide

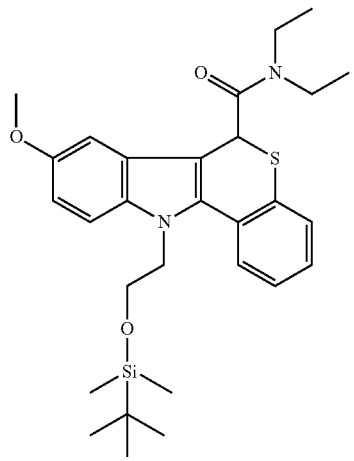 [SMILES: CCN(CC)C(=O)C1Sc2ccccc2-c2c1c1cc(OC)ccc1n2CCO[Si](C)(C)C(C)(C)C]

To a solution of (+−)-8-methoxy-6,11-dihydro-5-thia-11-aza-benzo[a]fluorene-6-carboxylic acid diethyl amide Example 1(ii) (2.0 g, 5.40 mmol) in anhydrous DMF (20 ml) was added sodium hydride 60% dispersion in mineral oil (240 mg, 6.0 mmol) and the mixture stirred at room temperature for 5 min under nitrogen. 2-(bromoethoxy)-tert-butyl-dimethylsilane (2.6 g, 10.8 mmol) was added and the mixture stirred for 4 h. The solvents were removed in vacuo, the residue quenched with water (30 ml), extracted with DCM (2×30 ml), dried (MgSO$_4$) and solvents removed in vacuo. The residue was purified by column chromatography on silica, eluting with 3% EtOAc/CH$_2$Cl$_2$ to give the title compound (2.0 g, 70%) as a yellow solid.

Example 5(ii). (+−) 11-[2-hydroxyethyl]-8-hydroxy-6,11-dihydro-5-thia-11-aza-benzo[a]fluorene-6-carboxylic acid diethylamide

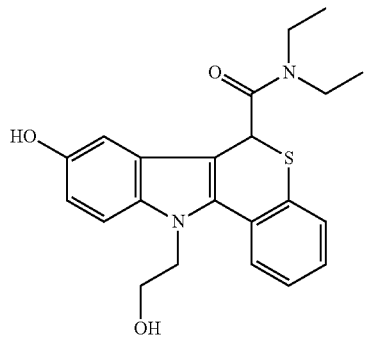 [SMILES: CCN(CC)C(=O)C1Sc2ccccc2-c2c1c1cc(O)ccc1n2CCO]

To a solution of (+−) 11-[2-(tertbutyl-dimethyl-silanyloxy)]ethyl]-8-methoxy-6,11-dihydro-5-thia-11-aza-benzo[a]fluorene-6-carboxylic acid diethylamide (1.0 g, 1.91 mmol) in dry DCM (60 ml) at −78° C. was added boron tribromide (11.5 ml, 1M in DCM, 11.5 mmol). The solution was allowed to rise to RT and stirred for 24 h. The solvents were removed in vacuo, quenched with methanol (40 ml), and 1NHCl (10 ml) added, refluxed for 1 h. The solvents were removed in vacuo, the mixture was dissolved methanol (5 ml), quenched with water (100 ml), filtered, dried in vacuo (45° C.) to give the title compound (0.77 g, 100%) as a light brown powder.

Example 5(iii): (+−) 11-[2-hydroxyethyl]-8-ethoxy-6,11-dihydro-5-thia-11-aza-benzo[a]fluorene-6-carboxylic acid diethylamide

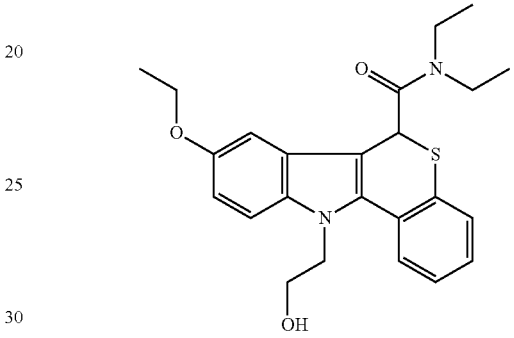

To a solution of (+−) 11-[2-hydroxyethyl]-8-hydroxy-6,11-dihydro-5-thia-11-aza-benzo[a]fluorene-6-carboxylic acid diethylamide (400 mg, 1.01 mmol) in anhydrous DMF (4 ml) at 0° C. was added sodium hydride 60% dispersion in mineral oil (40 mg, 1.01 mmol). The mixture was stirred at 0° C. for 10 min under nitrogen. Ethyl bromide (218 mg, 2.0 mmol, 150 ul) was added and the mixture stirred for 24 h. The solvents were removed in vacuo, the residue quenched with water (30 ml), extracted with DCM (2×30 ml), dried (MgSO$_4$) and solvents removed in vacuo. The residue was purified by column chromatography on silica, eluting with 40-60% EtOAc/CH$_2$Cl$_2$ to give the title compound (340 mg, 79%) as a white solid.

Example 5(iv): (+−) 11-[2-methanesulphoxyethyl]-8-ethoxy-6,11-dihydro-5-thia-11-aza-benzo[a]fluorene-6-carboxylic acid diethylamide

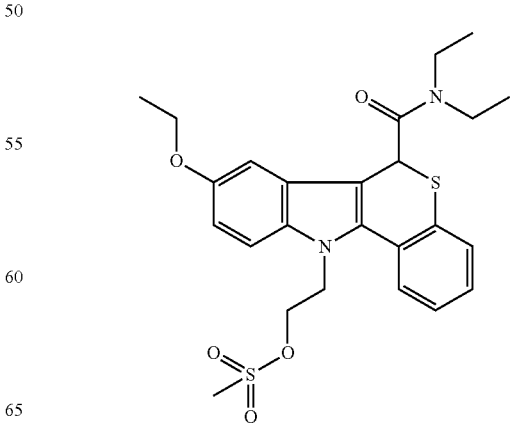

To a suspension of (+-) 11-[2-hydroxyethyl]-8-ethoxy-6,11-dihydro-5-thia-11-aza-benzo[a]fluorene-6-carboxylic acid diethylamide (0.34 g, 0.80 mmol) in anhydrous DCM (15 ml) was added pyridine (0.63 g, 8.0 mmol, 0.65 ml). The reaction was cooled to 0° C. and methane sulfonyl chloride (0.37 g, 3.2 mmol, 0.25 ml) was added. The reaction mixture was stirred at RT for 3 h. The mixture was washed with 0.5M HCl (2×20 ml), then water 2×20 ml), dried (MgSO$_4$) and the solvent removed under reduced pressure. The residue was purified by column chromatography on silica, eluting with 20% EtOAc/CH$_2$Cl$_2$ The residue was quenched with ether/pet. spirit, filtered, dried in vacuo (45° C.) to give the title compound (0.38 g, 95%) as a pale yellow solid.

Example 5(v). (+-) 11-[2-fluoroethyl]-8-ethoxy-6,11-dihydro-5-thia-11-aza-benzo[a]fluorene-6-carboxlic acid diethylamide

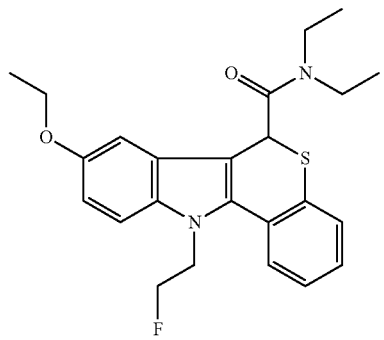 [SMILES: CCOc1ccc2c(c1)c1c(n2CCF)-c2ccccc2SC1C(=O)N(CC)CC]

To a solution of (+-) 11-[2-methanesulphoxyethyl]-8-ethoxy-6,11-dihydro-5-thia-11-aza-benzo[a]fluorene-6-carboxylic acid diethylamide (100 mg, 0.20 mmol) in anhydrous acetonitrile (5 ml) under nitrogen was added TBAF 1.0 M in THF (0.4 ml, 0.4 mmol). The mixture was heated to 80° C. for 2 h. The solvents were removed in vacuo and the residue purified by column chromatography on silica eluting with 5-10% EtOAc/CH$_2$Cl$_2$ to give the title compound (26 mg, 31%) as a yellow solid.

Example 6

Preparation of (+-)7-methoxy-11-(2-fluoroethyl)-6,11-dihydro-5-thia-11-aza-benzo[a]fluorene-6-carboxylic acid diethyl amide (non-radioactive imaging agent 2) and (+-)9-methoxy-11-(2-fluoroethyl)-6,11-dihydro-5-thia-11-aza-benzo[a]fluorene-6-carboxylic acid diethyl amide (non-radioactive imaging agent 7)

Example 6(i). 7-methoxy-6,11-dihydro-5-thia-11-aza-benzo[a]fluorene-6-carboxylic acid diethylamide and 9-methoxy-6,11-dihydro-5-thia-11-aza-benzo[a]fluorene-6-carboxylic acid diethylamide

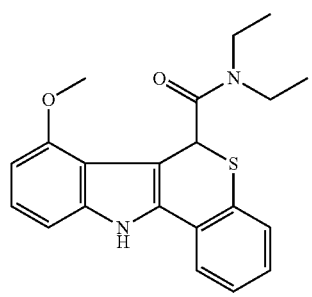

+

-continued

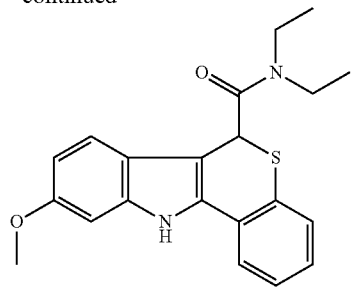

To a solution of (+-)-4-Oxo-thiochroman-2-carboxylic acid diethyl amide (3.33 g, 12.6 mmol) (Example 1(i)) and 3-methoxyphenyl hydrazine hydrochloride (2.2 g, 12.6 mmol) in ethanol (30 ml) was added concentrated sulphuric acid (1.83 ml, 3.40 g, 11.5 mmol) under nitrogen. The reaction mixture was heated under reflux for 24 h. After cooling, the reaction mixture was filtered, the solid washed with ethanol, dried in vacuo (45° C.) to give a mixture of 7-methoxy-6,11-dihydro-5-thia-11-aza-benzo[a]fluorene-6-carboxylic acid diethylamide and 9-methoxy-6,11-dihydro-5-thia-11-aza-benzo[a]-fluorene-6-carboxylic acid diethylamide (3.2 g, 69%) as a pale white solid.

Example 6(ii): 11-(2-fluoroethyl)-7-methoxy-6,11-dihydro-5-thia-11-aza-benzo[a]fluorene-6-carboxylic acid diethylamide and 11-(2-fluoroethyl)-9-methoxy-6,11-dihydro-5-thia-11-aza-benzo[a]fluorene-6-carboxylic acid diethylamide

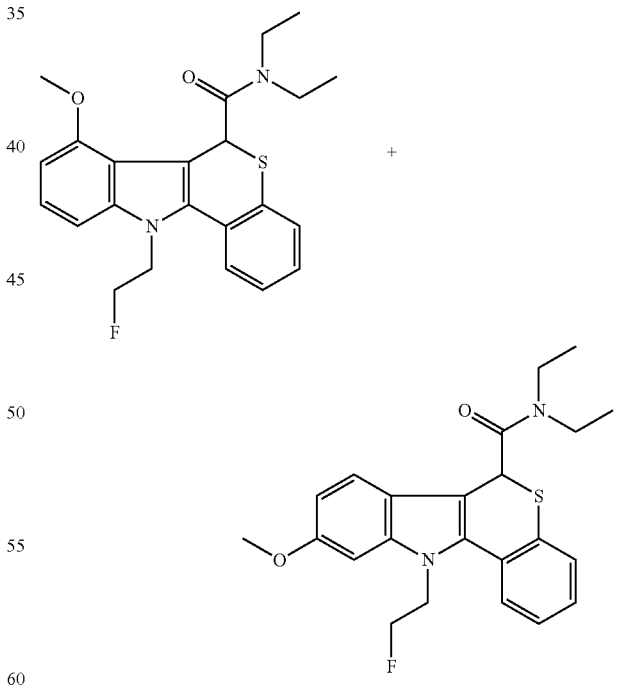

To a solution of mixture isomers 7-methoxy-6,11-dihydro-5-thia-11-aza-benzo[a]fluorene-6-carboxylic acid diethylamide and 9-methoxy-6,11-dihydro-5-thia-11-aza-benzo[a]-fluorene-6-carboxylic acid diethylamide (1.0 g, 2.73 mmol) (prepared according to Example 6(i)) in anhydrous DMF (10 ml) was added 2-fluoroethyl tosylate (1.2 g, 5.46 mmol) followed by sodium hydride 60% dispersion in mineral oil (131 mg, 5.46 mmol) under nitrogen. The reaction mixture was heated at 80° C. for 1 h. After cooling, the solvents were removed in vacuo, the residue quenched with water (30 ml), extracted with DCM (2×30 ml), dried (MgSO₄) and solvents removed in vacuo. The residue was purified by column chromatography on silica, eluting with 5-10% EtOAc/CH₂Cl₂ to give the isomer mixture (1.0g, 89%). The material (400 mg) was then purified by HPLC eluting with water (A) and methanol (B) (Gemini 5u, C18, 110A, 150×21 mm, 70-95% B over 20 mm, 21 mL/min) to afford 240 mg of 9-methoxy-6,11-dihydro-5-thia-11-aza-benzo[a]fluorene-6-carboxylic acid diethylamide as a yellow solid and 100 mg of 7-methoxy-6,11-dihydro-5-thia-11-aza-benzo[a]fluorene-6-carboxylic acid diethylamide as a white solid.

Example 7

Preparation of ¹⁸F-labelled Imaging Agents 2 and 7

Example 7(i): 11-[2-tertbutyl-dimethyl-silanyloxy)]ethyl]-7-methoxy-6,11-dihydro-5-thia-11-aza-benzo[a]fluorene-6-carboxylic acid diethylamide and 11-[2-(tertbutyl-dimethyl-silanyloxy)]ethyl]-9-methoxy-6,11-dihydro-5-thia-11-aza-benzo[a]fluorene-6-carboxylic acid diethylamide To a solution of the mixture of isomers prepared according to Example 6(i) (2.0 g, 5.46 mmol) in anhydrous DMF (20 ml) was added sodium hydride 60% dispersion in mineral oil (240 mg, 6.0 mmol) and the mixture stirred at room temperature for 5 min under nitrogen. 2-(bromoethoxy)-tert-butyl-dimethylsilane (2.6 g, 10.9 mmol) was added and the mixture stirred for 4 h. The solvents were removed in vacuo, the residue quenched with water (30 ml), extracted with DCM (2×30 ml), dried (MgSO₄) and solvents removed in vacuo. The residue was purified by column chromatography on silica, eluting with 5% EtOAc/CH₂Cl₂ to give the isomer mixture 11-[2-(tertbutyl-dimethyl-silanyloxy)]ethyl]-7-methoxy-6,11-dihydro-5-thia-11-aza-benzo[a]fluorene-6-carboxylic acid diethylamide and 11-[2-(tertbutyl-dimethyl-silanyloxy)]ethyl]-9-methoxy-6,11-dihydro-5-thia-11-aza-benzo[a]fluorene-6-carboxylic acid diethylamide (2.53 g, 88%) as a yellow solid.

Example 7(ii): 11-[2-hydroxyethyl]-7-methoxy-6,11-dihydro-5-thia-11-aza-benzo[a]fluorene-6-carboxylic acid diethylamide and 11-[2-(2-hydroxyoxy)]ethyl]-7-methoxy-6,11-dihydro-5-thia-11-aza-benzo[a]fluorene-6-carboxylic acid diethylamide

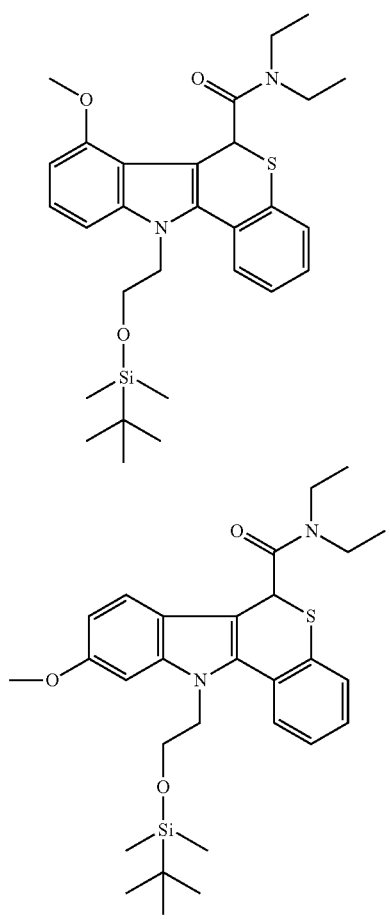

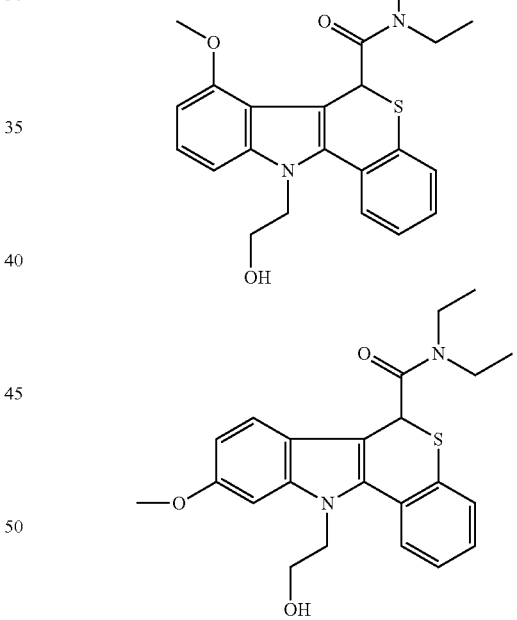

To a solution of mixture isomers prepared according to Example 7(i) (2.5 g, 4.76 mmol) in anhydrous THF (40 ml) was added TBAF 1.0 M in THF (9.5 ml, 9.5 mmol) under nitrogen. The mixture was stirred at room temperature for 4 h. The solvents were removed in vacuo, the residue was purified by column chromatography on silica, eluting with 40% EtOAc/CH₂Cl₂ to give the isomer mixture 11-[2-hydroxyethyl]-7-methoxy-6,11-dihydro-5-thia-11-aza-benzo[a]fluorene-6-carboxylic acid diethylamide and 11-[2-(2-hydroxyoxy)]ethyl]-7-methoxy-6,11-dihydro-5-thia-11-aza-benzo[a]fluorene-6-carboxylic acid diethylamide (1.90 g, 97%) as a pale yellow solid.

Example 7(iii): (+-) 11-[2-methanesulphoxyethyl]-7-methoxy-6,11-dihydro-5-thia-11-aza-benzo[a]fluorene-6-carboxylic acid diethylamide and (+-) 11-2-(methanesulphoxyethyl)-9-methoxy-6,11-dihydro-5-thia-11-aza-benzo[a]fluorene-6-carboxylic acid diethylamide

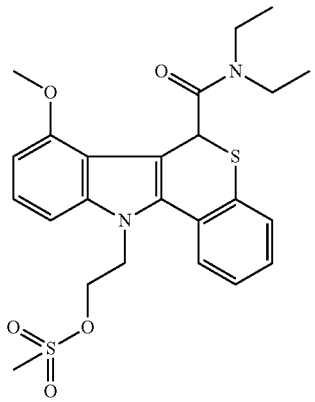

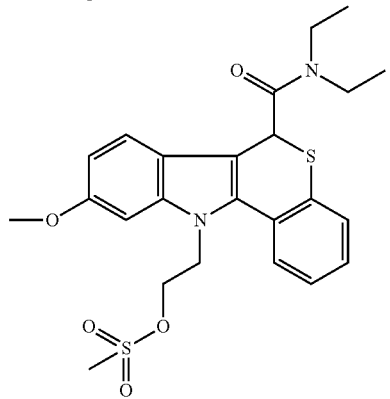

To a solution of mixture isomers prepared according to Example 7(ii) (1.0 g, 2.4 mmol) dissolved in anhydrous DCM (30 ml) was added pyridine (1.9 g, 24.0 mmol, 1.9 ml). The reaction was cooled to 0° C. and methane sulfonyl chloride (1.1 g, 9.6 mmol, 0.74 ml) was added. The reaction mixture was stirred at RT for 4 h. The mixture was washed with 0.5M HCl (2×20 ml), then water 2×20 ml), dried (MgSO$_4$) and the solvent removed under reduced pressure. The residue was purified by column chromatography on silica, eluting with 20% EtOAc/CH$_2$Cl$_2$ to give the isomer mixture (1.0 g, 85%). The material (400 mg) was then purified by HPLC eluting with water (A) and methanol (B) (Gemini 5u, C18, 110A, 150×21 mm, 5-95% B over 30 min, 21 mL/min) to afford 170 mg of 11-[2-methanesulphoxyethyl]-7-methoxy-6,11-dihydro-5-thia-11-aza-benzo[a]fluorene-6-carboxylic acid diethylamide as a white solid and 60mg of 11-2-(methanesulphoxyethyl)-9-methoxy-6,11-dihydro-5 -thia-11-aza-benzo[a]fluorene-6-carboxylic acid diethylamide as a white solid.

Example 7(iv): Direct labeling method

The precursor compounds 11-[2-methanesulphoxyethyl]-7-methoxy-6,11-dihydro-5-thia-11-aza-benzo[a]fluorene-6-carboxylic acid diethylamide and 11-2-(methanesulphoxyethyl)-9-methoxy-6,11-dihydro-5-thia-11-aza-benzo[a]fluorene-6-carboxylic acid diethylamide, prepared according to Example 7(iii) were radiolabelled by a direct labeling method to obtain imaging agents 2 and 7, respectively. $^{18}$F water was added to the reaction vessel followed by K222 (2mg) in acetonitrile (500 ul), and KHCO$_3$ (0.1 mol dm$^{-3}$, 50 ul) and dried at 100° C. for 20-30 mins. The precursor (0.5-1 mg) in acetonitrile (1000 ul) was added. The reaction vessel was sealed and heated at 100° C. for 10 mins. The reaction mixture was cooled, washed from the reaction vessel with water (1.5 ml) and purified on a semi preperative HPLC. The fraction containing the main radioactive product was collected and diluted to a volume of 10 ml with H$_2$O. This was loaded onto a conditioned light C18 sep pak, flushed with H$_2$O (1×2 ml), and the product eluted with EtOH (0.5 ml) into a P6 vial and PBS(5 ml) was added.

Example 8

Preparation $^{18}$F-labelled Imaging Agents 1, 3, 4 and 5

Example 8(i): Preparation of Precursor Compounds

The precursor compounds:
(a) (+-)-8-methoxy-6,11-dihydro-5-thia-11-aza-benzo[a]fluorene-6-carboxylic acid diethyl amide (prepared according to Example 1(ii));
(b) (+-)-10-methoxy-6,11-dihydro-5-thia-11-aza-benzo[a]fluorene-6-carboxylic acid diethyl amide (prepared according to Example 2(i));
(c) (+-)-4-Fluoro-6,11-dihydro-5-thia-11azabenzo[a]fluorene-6-carboxylic acid diethylamide (prepared according to Example 3(iii)); and,
(d) (+-) 3-Fluoro-11-(2-fluoro-ethyl)-6,11-dihydro-5-thia-11-aza-benzo[a]fluorene-6-carboxylic acid diethylamide (prepared according to Example 4(iv))

were radiolabelled using the indirect labeling method described below to obtain $^{18}$F-labelled imaging agents 1, 3, 4 and 5, respectively.

Example 8(ii): Indirect labeling method $^{18}$F/water was added to K222 (4 mg), aqueous K$_2$CO$_3$ (50 μl of a 0.1 molar solution) and acetonitrile (500 μl) in a reaction vessel and dried for 20-30 mins at 100° C. under a stream of nitrogen. Ethyl-1,2-ditosylate (4 mg) in acetonitrile (1000 ul) was added and heated at 100° C. for 10 mins. The reaction mixture was cooled and purified by semi preperative HPLC and the fraction containing $^{18}$F-fluoroethyl tosylate was collected. This fraction was diluted to a volume of ca.20 ml with H$_2$O, loaded onto a conditioned light t-C18 sep pak, and flushed with H$_2$O (1×2 ml). The sep pak was dried on the N$_2$ line with high flow, for 20 mins. The $^{18}$F fluoroethyl tosylate was then eluted with DMF(500 μl).

Separately, the precursor (13 mg) in DMF(250 ul) was added to a second reaction vessel, and purged with N$_2$, for 5 mins. NaH(1.3 mg) in DMF(2×250 ul) was then added under nitrogen and the reaction vessel was heated at 45° C. for 0.5-1 h. To this was then added the $^{18}$F fluoroethyl tosylate in DMF prepared above and heated at 100° C. for 10 mins in the N$_2$ purged reaction vessel. The reaction was cooled and washed from the reaction vessel with water (1 ml). The solution was filtered through a syringe filter and purified on a preparative HPLC. The fraction containing the main radioactive peak was collected. This was diluted to a volume of ca.10 ml with H$_2$O, and loaded onto a conditioned light C18 sep pak, flushed with $H_2O$ (1×2 ml), and eluted with EtOH (0.5 ml) into a P6 vial and Phosphate Buffered Saline (5 ml) added.

Example 9

Preparation of $^{18}F$-labelled Imaging Agent 6

(+-) 11-[2-methanesulphoxyethyl]-8-ethoxy-6,11-dihydro-5-thia-11-aza-benzo[a]fluorene-6-carboxylic acid diethylamide (prepared according to Example 5(iv)) was radiolabelled using the direct labeling method described in Example 7(iv) above.

Example 10

In Vitro Potency Assay

The compounds were screened for their affinity for PBR using a method adapted from Le Fur et al (Life Sci. 1983; USA 33: 449-57).

The compounds to be tested (dissolved in 50mM Tris-HCl, pH 7.4, 10 mM $MgCl_2$ containing 1% DMSO) competed for binding to Wistar rat heart PBR against 0.3 nM [$^3H$]-PK-11195. The reaction was carried out in 50 mM Tris-HCl, pH 7.4 10 mM $MgCl_2$ for 15 minutes at 25° C.

The compounds were screened at 6 different concentrations over a 300-fold range of concentrations around the estimated Ki. The results are presented in Table 1 above, and demonstrate that the potency of the compounds of the invention favourably compares with that of the prior art compounds.

Example 11

In Vivo Biodistribution Method

In vivo imaging agents 1-7 as prepared in Examples 7, 8 and 9 above were tested in the in vivo biodistribution model and their biodistribution compared to that of the prior art compound [$^{18}F$]FE-PBR (prepared according to Example 14 of WO 2007/057705).

Adult male Wistar rats (200-300 g) were injected with 1-3 MBq of each in vivo imaging agent via the lateral tail vein. At 2 10,30 or 60 min (n=3) after injection, rats were euthanised and tissues or fluids were sampled for radioactive measurement by liquid scintillation counting.

As compared with [$^{18}F$]FE-PBR, the compounds of the invention demonstrated a higher olfactory bulb:striatum ratio of binding (see Table 1 above).

Example 12

Autoradiography Using Facial Nerve Axotomy (FNA) Model

For in vivo studies, male Wistar rats (180-200 g) were used. Under Isoflurane anaesthesia, the hair from the right side of the auricular region was removed. An infraauricular incision was made and the main trunk of the facial nerve identified. The facial nerve was severed behind the ear at the exit from the stylomastoid foramen. The wound was sutured and animals left to recover. Seven days post-surgery animals were injected with ~5-10 MBq in vivo imaging agent 1 via the lateral tail vein. Animals were killed 30 minutes later and brain stem removed and frozen in isopentane. Cryostat sections (12 μm) of brainstem containing both facial nuclei were mounted on glass slides and exposed to phosphor screen overnight.

Screens were then scanned on the Storm (GE Healthcare) phosphor-imager and the resultant scan was analysed and quantified using ImageQuant TL (GE Healthcare). FIGS. 1 and 2 illustrate the data obtained in this experiment.

What is claimed is:

1. An in vivo imaging agent which is selected from:

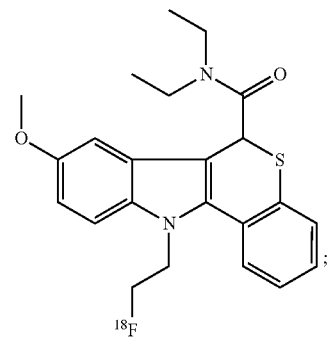

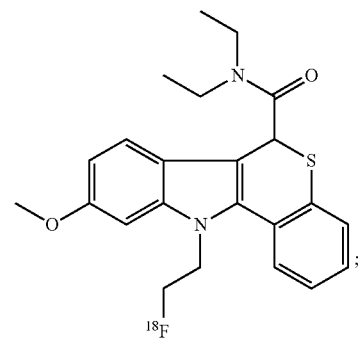

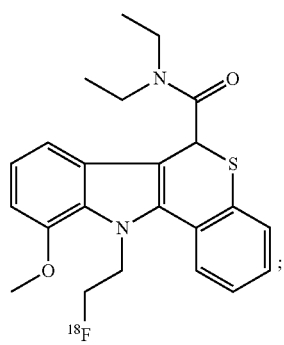

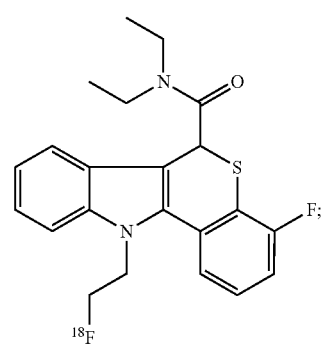

2. A precursor compound useful for the preparation of an in vivo imaging compound, wherein said imaging compound is selected from:

-continued
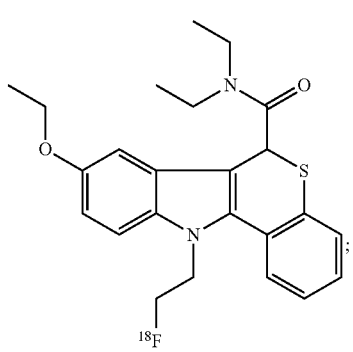
6
and
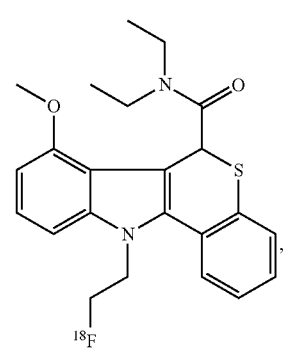
7
and said precursor compound is selected from:
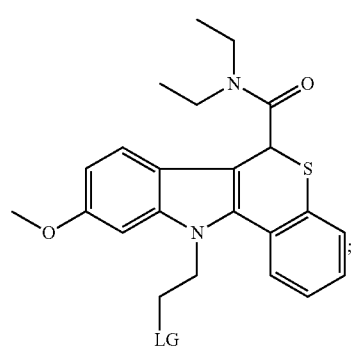
1'
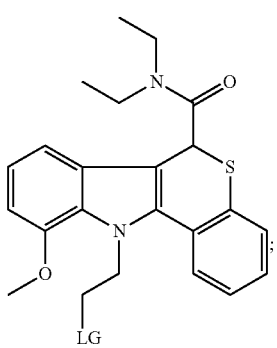
-continued
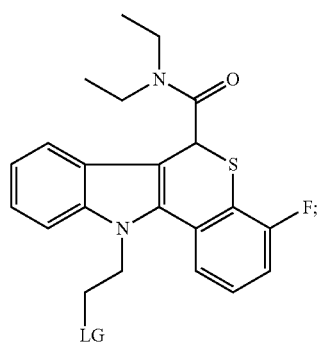
3'
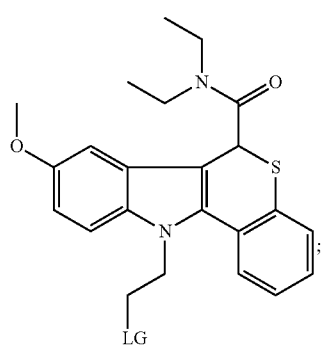
4'
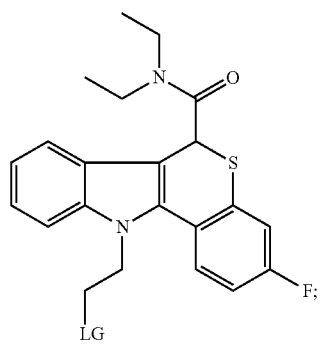
5'
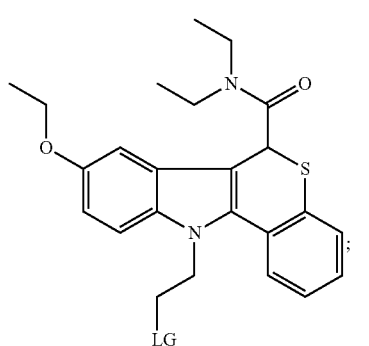
2'
6'
and -continued
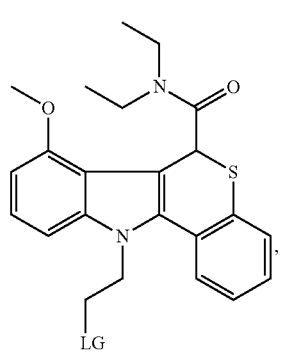
wherein LG is selected from the group consisting of Cl, Br, I, tosylate (OTs), mesylate (OMs), and triflate.
3. A radiopharmaceutical composition comprising an in vivo imaging agent as defined in claim 1, together with a biocompatible carrier in a form suitable for mammalian administration.
* * * * *